United States Patent
Scheib et al.

(10) Patent No.: US 12,181,579 B2
(45) Date of Patent: Dec. 31, 2024

(54) CONTROLLING AN EMITTER ASSEMBLY PULSE SEQUENCE

(71) Applicant: Cilag GmbH International, Zug (CH)

(72) Inventors: Charles J. Scheib, Loveland, OH (US); Joshua D. Talbert, Cottonwood Heights, UT (US); Jeffrey S. Swayze, West Chester, OH (US)

(73) Assignee: Cilag GmbH International, Zug (CH)

( * ) Notice: Subject to any disclaimer, the term of this patent is extended or adjusted under 35 U.S.C. 154(b) by 258 days.

(21) Appl. No.: 16/128,180

(22) Filed: Sep. 11, 2018

(65) Prior Publication Data
US 2020/0015900 A1 Jan. 16, 2020

Related U.S. Application Data

(60) Provisional application No. 62/698,625, filed on Jul. 16, 2018.

(51) Int. Cl.
*G01S 17/36* (2006.01)
*A61B 1/00* (2006.01)
(Continued)

(52) U.S. Cl.
CPC .......... *G01S 17/36* (2013.01); *A61B 1/00006* (2013.01); *A61B 1/000094* (2022.02);
(Continued)

(58) Field of Classification Search
CPC .......... A61B 17/0482; A61B 17/00234; A61B 17/0218; A61B 17/0469; A61B 17/0483;
(Continued)

(56) References Cited

U.S. PATENT DOCUMENTS 3,901,602 A 8/1975 Gravatt, Jr.
4,753,641 A 6/1988 Vaslow
(Continued)

FOREIGN PATENT DOCUMENTS

CN 109011149 A 12/2018
DE 102015115903 A1 3/2017
(Continued)

OTHER PUBLICATIONS

Kurata et al. "Time-of-flight Near-infrared Spectroscopy for Non-destructive Measurement of Internal Quality in Grapefruit," J. Amer. Soc. Hort. Sci. 138(3): 225-228, 2013.
(Continued)

*Primary Examiner* — John D Li

(57) ABSTRACT

A system and method for controlling an emitter assembly for visualizing a surgical site is disclosed. The emitter assembly is configured to emit a pulse pattern of electromagnetic radiation at the surgical site. The electromagnetic radiation pattern can include infrared radiation, visible light, or combinations thereof in either structured or non-structured formats. Further, a receiver assembly is configured to receive the electromagnetic radiation reflected from the surgical site. The control circuit can be configured to control the sequence or pattern in which the electromagnetic radiation is pulsed according to a preset sequence or according to feedback from the surgical site.

27 Claims, 25 Drawing Sheets

(51) Int. Cl.

| | |
|---|---|
| *A61B 1/005* | (2006.01) |
| *A61B 1/04* | (2006.01) |
| *A61B 1/045* | (2006.01) |
| *A61B 1/05* | (2006.01) |
| *A61B 1/06* | (2006.01) |
| *A61B 1/07* | (2006.01) |
| *A61B 1/313* | (2006.01) |
| *A61B 5/00* | (2006.01) |
| *A61B 17/00* | (2006.01) |
| *A61B 17/02* | (2006.01) |
| *A61B 17/04* | (2006.01) |
| *A61B 17/06* | (2006.01) |
| *A61B 17/062* | (2006.01) |
| *A61B 17/064* | (2006.01) |
| *A61B 17/11* | (2006.01) |
| *A61B 17/115* | (2006.01) |
| *A61B 17/34* | (2006.01) |
| *A61B 34/00* | (2016.01) |
| *A61B 34/20* | (2016.01) |
| *A61B 34/30* | (2016.01) |
| *A61B 34/32* | (2016.01) |
| *A61B 90/00* | (2016.01) |
| *A61B 90/13* | (2016.01) |
| *A61B 90/30* | (2016.01) |
| *A61B 90/35* | (2016.01) |
| *G02F 1/13* | (2006.01) |
| *G06T 1/00* | (2006.01) |
| *A61B 34/10* | (2016.01) |

(52) U.S. Cl.
CPC ...... *A61B 1/00013* (2013.01); *A61B 1/00043* (2013.01); *A61B 1/00045* (2013.01); *A61B 1/00096* (2013.01); *A61B 1/00149* (2013.01); *A61B 1/00194* (2022.02); *A61B 1/009* (2022.02); *A61B 1/04* (2013.01); *A61B 1/045* (2013.01); *A61B 1/046* (2022.02); *A61B 1/05* (2013.01); *A61B 1/051* (2013.01); *A61B 1/06* (2013.01); *A61B 1/0605* (2022.02); *A61B 1/0607* (2013.01); *A61B 1/063* (2013.01); *A61B 1/0638* (2013.01); *A61B 1/0661* (2013.01); *A61B 1/07* (2013.01); *A61B 1/3132* (2013.01); *A61B 5/0036* (2018.08); *A61B 5/0086* (2013.01); *A61B 5/0095* (2013.01); *A61B 17/00234* (2013.01); *A61B 17/0218* (2013.01); *A61B 17/0469* (2013.01); *A61B 17/0482* (2013.01); *A61B 17/0483* (2013.01); *A61B 17/06066* (2013.01); *A61B 17/062* (2013.01); *A61B 17/064* (2013.01); *A61B 17/1114* (2013.01); *A61B 17/1155* (2013.01); *A61B 17/3423* (2013.01); *A61B 34/20* (2016.02); *A61B 34/30* (2016.02); *A61B 34/32* (2016.02); *A61B 34/73* (2016.02); *A61B 90/03* (2016.02); *A61B 90/13* (2016.02); *A61B 90/30* (2016.02); *A61B 90/35* (2016.02); *A61B 90/36* (2016.02); *A61B 90/361* (2016.02); *A61B 90/37* (2016.02); *G02F 1/1326* (2013.01); *G06T 1/0007* (2013.01); *A61B 1/00009* (2013.01); *A61B 1/0676* (2013.01); *A61B 2017/00061* (2013.01); *A61B 2017/00119* (2013.01); *A61B 2017/00367* (2013.01); *A61B 2017/00477* (2013.01); *A61B 2017/00876* (2013.01); *A61B 2034/105* (2016.02); *A61B 2034/107* (2016.02); *A61B 2034/2051* (2016.02); *A61B 2034/2055* (2016.02); *A61B 2034/2057* (2016.02); *A61B 2034/2063* (2016.02); *A61B 2034/2065* (2016.02); *A61B 34/25* (2016.02); *A61B 2034/301* (2016.02); *A61B 2034/302* (2016.02); *A61B 2090/061* (2016.02); *A61B 2090/064* (2016.02); *A61B 2090/306* (2016.02); *A61B 2090/367* (2016.02); *A61B 2090/373* (2016.02); *A61B 2090/374* (2016.02); *A61B 2090/3762* (2016.02); *A61B 2090/378* (2016.02); *A61B 2505/05* (2013.01); *A61B 2560/0462* (2013.01); *A61B 2576/00* (2013.01)

(58) Field of Classification Search
CPC ............ A61B 17/06066; A61B 17/062; A61B 17/064; A61B 17/1114; A61B 17/1155; A61B 17/3423; A61B 34/20; A61B 34/30; A61B 34/32; A61B 34/73; A61B 90/03; A61B 90/13; A61B 90/30; A61B 90/35; A61B 90/36; A61B 90/361; A61B 90/37; A61B 5/0036; A61B 5/0086; A61B 5/0095; A61B 1/00006; A61B 1/00043; A61B 1/00045; A61B 1/00096; A61B 1/00149; A61B 1/04; A61B 1/045; A61B 1/05; A61B 1/051; A61B 1/06; A61B 1/0607; A61B 1/063; A61B 1/0638; A61B 1/0661; A61B 1/07; A61B 1/3132; A61B 1/00009; A61B 1/0676; A61B 2034/105; A61B 2034/107; A61B 2034/2051; A61B 2034/2055; A61B 2034/2057; A61B 2034/2063; A61B 2034/2065; A61B 2034/301; A61B 2034/302; A61B 2090/061; A61B 2090/064; A61B 2090/306; A61B 2090/367; A61B 2090/373; A61B 2090/374; A61B 2090/3762; A61B 2090/378; A61B 2017/00061; A61B 2017/00119; A61B 2017/00367; A61B 2017/00477; A61B 2017/00876; A61B 2505/05; A61B 2560/0462; A61B 2576/00
See application file for complete search history.

(56) References Cited

U.S. PATENT DOCUMENTS

| | | |
|---|---|---|
| 4,785,180 A | 11/1988 | Dietrich et al. |
| 4,986,262 A | 1/1991 | Saito |
| 5,434,667 A | 7/1995 | Hutchins et al. |
| 5,460,182 A | 10/1995 | Goodman et al. |
| 5,609,562 A | 3/1997 | Kaali |
| 6,350,233 B1 | 2/2002 | Lubowski |
| 6,386,758 B2 | 5/2002 | Loser |
| 6,614,453 B1 | 9/2003 | Suri et al. |
| 6,632,183 B2 | 10/2003 | Bowman et al. |
| 6,804,012 B2 | 10/2004 | Gombert |
| 6,869,430 B2 | 3/2005 | Balbierz et al. |
| 6,951,535 B2 | 10/2005 | Ghodoussi et al. |
| 7,137,980 B2 | 11/2006 | Buysse et al. |
| 7,314,048 B2 | 1/2008 | Couture et al. |
| 7,477,931 B2 | 1/2009 | Hoyt |
| 7,516,675 B2 | 4/2009 | Kurtz et al. |
| 7,726,171 B2 | 6/2010 | Langlotz et al. |
| 7,740,623 B2 | 6/2010 | Nayak et al. |
| 7,766,210 B2 | 8/2010 | Shelton, IV et al. |
| 7,770,775 B2 | 8/2010 | Shelton, IV et al. |
| 7,798,385 B2 | 9/2010 | Boyden et al. |
| 7,810,691 B2 | 10/2010 | Boyden et al. |
| 7,901,353 B2 | 3/2011 | Vayser et al. |
| 7,905,840 B2 | 3/2011 | Pimenta et al. |
| 7,975,894 B2 | 7/2011 | Boyden et al. |
| 8,041,089 B2 | 10/2011 | Drumm et al. |
| 8,063,883 B2 | 11/2011 | Senft et al. |
| 8,073,528 B2 | 12/2011 | Zhao et al. |

(56) References Cited

U.S. PATENT DOCUMENTS

| | | |
|---|---|---|
| 8,079,950 B2 | 12/2011 | Stern et al. |
| 8,142,450 B2 | 3/2012 | Harris et al. |
| 8,161,977 B2 | 4/2012 | Shelton, IV et al. |
| 8,224,484 B2 | 7/2012 | Swarup et al. |
| 8,231,639 B2 | 7/2012 | Bolduc et al. |
| 8,523,043 B2 | 9/2013 | Ullrich et al. |
| 8,632,468 B2 | 1/2014 | Glossop et al. |
| 8,652,148 B2 | 2/2014 | Zuhars |
| 8,706,211 B2 | 4/2014 | Dacey, Jr. et al. |
| 8,755,576 B2 | 6/2014 | Taerum |
| 8,763,879 B2 | 7/2014 | Shelton, IV et al. |
| 8,820,603 B2 | 9/2014 | Shelton, IV et al. |
| 8,840,616 B2 | 9/2014 | Wilkinson et al. |
| 8,932,208 B2 | 1/2015 | Kendale et al. |
| 8,934,003 B2 | 1/2015 | Popovic et al. |
| 8,989,528 B2 | 3/2015 | Udd |
| 8,992,558 B2 | 3/2015 | Stone et al. |
| 9,005,118 B2 | 4/2015 | Selover et al. |
| 9,044,230 B2 | 6/2015 | Morgan et al. |
| 9,064,173 B2 | 6/2015 | Redden |
| 9,072,501 B2 | 7/2015 | Menchaca et al. |
| 9,072,535 B2 | 7/2015 | Shelton, IV et al. |
| 9,119,670 B2 | 9/2015 | Yang et al. |
| 9,141,868 B2 | 9/2015 | Xu et al. |
| 9,161,817 B2 | 10/2015 | Olson et al. |
| 9,161,820 B2 | 10/2015 | Mark et al. |
| 9,179,822 B2 | 11/2015 | Kitamura et al. |
| 9,179,890 B2 | 11/2015 | Ionasec et al. |
| 9,241,693 B2 | 1/2016 | Taylor et al. |
| 9,254,103 B2 | 2/2016 | Krishnaswamy et al. |
| 9,259,290 B2 | 2/2016 | Jenkins et al. |
| 9,265,587 B2 | 2/2016 | Vancamberg et al. |
| 9,274,047 B2 | 3/2016 | Velten et al. |
| 9,282,878 B2 | 3/2016 | Grey et al. |
| 9,295,773 B2 | 3/2016 | Prosl et al. |
| 9,326,770 B2 | 5/2016 | Shelton, IV et al. |
| 9,345,389 B2 | 5/2016 | Nie et al. |
| 9,402,726 B2 | 8/2016 | Linderman et al. |
| 9,480,534 B2 | 11/2016 | Bowling et al. |
| 9,547,940 B1 | 1/2017 | Sun et al. |
| 9,561,019 B2 | 2/2017 | Mihailescu et al. |
| 9,561,082 B2 | 2/2017 | Yen et al. |
| 9,597,054 B2 | 3/2017 | Kudavelly et al. |
| 9,649,109 B2 | 5/2017 | Ranucci et al. |
| 9,720,076 B2 | 8/2017 | Guo et al. |
| 9,730,690 B2 | 8/2017 | Shanley et al. |
| 9,760,989 B2 | 9/2017 | Yin et al. |
| 9,775,497 B2 | 10/2017 | Igarashi et al. |
| 9,788,851 B2 | 10/2017 | Dannaher et al. |
| 9,801,685 B2 | 10/2017 | Nguyen et al. |
| 9,855,317 B2 | 1/2018 | Bright |
| 9,857,167 B2 | 1/2018 | Jovanovski et al. |
| 9,883,857 B2 | 2/2018 | Shluzas et al. |
| 9,901,409 B2 | 2/2018 | Yang et al. |
| 9,911,187 B2 | 3/2018 | Steinle et al. |
| 9,918,640 B2 | 3/2018 | Ntziachristos et al. |
| 9,987,019 B2 | 6/2018 | Sato |
| 10,010,326 B2 | 7/2018 | Sato |
| 10,022,199 B2 | 7/2018 | Gassner et al. |
| 10,042,150 B2 | 8/2018 | Brown |
| 10,045,763 B2 | 8/2018 | Sato |
| 10,068,173 B2 | 9/2018 | Vayser et al. |
| 10,070,929 B2 | 9/2018 | Tanji |
| 10,085,611 B2 | 10/2018 | Yabe et al. |
| 10,105,470 B2 | 10/2018 | Reasoner et al. |
| 10,123,706 B2 | 11/2018 | Elbaz et al. |
| 10,136,959 B2 | 11/2018 | Mintz et al. |
| 10,143,470 B2 | 12/2018 | Sato |
| 10,170,205 B2 | 1/2019 | Curd et al. |
| 10,194,981 B2 | 2/2019 | Margallo Balbas et al. |
| 10,194,990 B2 | 2/2019 | Amanatullah et al. |
| 10,219,738 B2 | 3/2019 | Monty et al. |
| 10,226,299 B2 | 3/2019 | Raffy et al. |
| 10,238,356 B2 | 3/2019 | Suzuki et al. |
| 10,255,723 B2 | 4/2019 | Thomas et al. |
| 10,314,463 B2 | 6/2019 | Agrawal et al. |
| 10,357,253 B2 | 7/2019 | Sato |
| 10,357,317 B2 | 7/2019 | Dupont et al. |
| 10,390,835 B2 | 8/2019 | Williams |
| 10,433,911 B2 | 10/2019 | Wang et al. |
| 10,467,752 B2 | 11/2019 | Tanji |
| 10,470,687 B2 | 11/2019 | Garbey et al. |
| 10,470,763 B2 | 11/2019 | Yates et al. |
| 10,506,991 B2 | 12/2019 | Govari |
| 10,510,149 B2 | 12/2019 | Cutu et al. |
| 10,512,518 B2 | 12/2019 | Vayser et al. |
| 10,531,074 B2 | 1/2020 | Wilson et al. |
| 10,546,423 B2 | 1/2020 | Jones et al. |
| 10,548,679 B2 | 2/2020 | Carlson et al. |
| 10,561,465 B2 | 2/2020 | Scholl et al. |
| 10,576,246 B2 | 3/2020 | Fischell et al. |
| 10,587,659 B2 | 3/2020 | Miller |
| 10,588,699 B2 | 3/2020 | Richmond et al. |
| 10,607,738 B2 | 3/2020 | Davidson et al. |
| 10,643,371 B2 | 5/2020 | Bharadwaj et al. |
| 10,666,928 B2 | 5/2020 | Liu |
| 10,687,797 B2 | 6/2020 | Stone et al. |
| 10,695,166 B2 | 6/2020 | Willis et al. |
| 10,702,186 B2 | 7/2020 | Amies et al. |
| 10,704,093 B2 | 7/2020 | Deng et al. |
| 10,743,868 B2 | 8/2020 | Shelton, IV et al. |
| 10,768,402 B2 | 9/2020 | Brown |
| 10,792,034 B2 | 10/2020 | Scheib et al. |
| 10,806,518 B2 | 10/2020 | Amanatullah |
| 10,813,700 B2 | 10/2020 | Amanatullah |
| 10,861,197 B2 | 12/2020 | Kobayashi |
| 10,866,783 B2 | 12/2020 | Atarot et al. |
| 10,881,458 B2 | 1/2021 | Fischell et al. |
| 10,898,064 B2 | 1/2021 | Atarot et al. |
| 10,925,465 B2 | 2/2021 | Tully et al. |
| 10,925,598 B2 | 2/2021 | Scheib et al. |
| 10,945,787 B2 | 3/2021 | Fischell et al. |
| 10,945,796 B2 | 3/2021 | Popovic et al. |
| 10,973,519 B2 | 4/2021 | Weir et al. |
| 10,980,420 B2 | 4/2021 | Fengler et al. |
| 10,986,999 B2 | 4/2021 | Frangioni et al. |
| 10,987,176 B2 | 4/2021 | Poltaretskyi et al. |
| 11,006,100 B1 | 5/2021 | Douglas |
| 11,020,016 B2 | 6/2021 | Wallace et al. |
| 11,058,501 B2 | 7/2021 | Tokarchuk et al. |
| 11,122,987 B2 | 9/2021 | Barash et al. |
| 11,183,141 B2 | 11/2021 | Yamada |
| 11,257,589 B2 | 2/2022 | Shelton, IV et al. |
| 11,269,173 B2 | 3/2022 | Komp et al. |
| 11,276,175 B2 | 3/2022 | Witte |
| 11,315,438 B1 | 4/2022 | Hannaford et al. |
| 11,410,259 B2 | 8/2022 | Harris et al. |
| 11,424,027 B2 | 8/2022 | Shelton, IV |
| 11,583,349 B2 | 2/2023 | Azizian et al. |
| 11,771,487 B2 | 10/2023 | Shelton, IV et al. |
| 2001/0012327 A1 | 8/2001 | Loser |
| 2003/0069591 A1 | 4/2003 | Carson et al. |
| 2004/0082842 A1 | 4/2004 | Lumba et al. |
| 2004/0106916 A1 | 6/2004 | Quaid et al. |
| 2004/0147926 A1 | 7/2004 | Iversen |
| 2004/0176751 A1 | 9/2004 | Weitzner et al. |
| 2004/0230199 A1 | 11/2004 | Jansen et al. |
| 2005/0113846 A1 | 5/2005 | Carson |
| 2005/0124975 A1 | 6/2005 | Law |
| 2005/0167621 A1 | 8/2005 | Zeng et al. |
| 2005/0177181 A1 | 8/2005 | Kagan et al. |
| 2005/0228291 A1* | 10/2005 | Chance ............... A61B 5/0042 600/407 |
| 2005/0279354 A1 | 12/2005 | Deutsch et al. |
| 2006/0013454 A1* | 1/2006 | Flewelling ........... A61B 5/7264 382/128 |
| 2006/0079841 A1 | 4/2006 | Duff et al. |
| 2006/0206007 A1 | 9/2006 | Bala |
| 2006/0224045 A1 | 10/2006 | Whipple et al. |
| 2006/0227324 A1 | 10/2006 | Bloom et al. |
| 2006/0282096 A1 | 12/2006 | Papa et al. |
| 2006/0293557 A1 | 12/2006 | Chuanggui et al. |
| 2007/0014784 A1 | 1/2007 | Nayak et al. |
| 2007/0019781 A1 | 1/2007 | Haras |

(56) References Cited

U.S. PATENT DOCUMENTS

| | | |
|---|---|---|
| 2007/0040906 A1 | 2/2007 | Iketani |
| 2007/0066970 A1 | 3/2007 | Ineson |
| 2007/0093748 A1 | 4/2007 | Nayak et al. |
| 2007/0100210 A1 | 5/2007 | Selover et al. |
| 2007/0123912 A1 | 5/2007 | Carson |
| 2007/0156021 A1 | 7/2007 | Morse et al. |
| 2007/0172472 A1 | 7/2007 | Nayak |
| 2007/0175955 A1 | 8/2007 | Shelton et al. |
| 2007/0239149 A1 | 10/2007 | Lieponis |
| 2007/0265495 A1 | 11/2007 | Vayser |
| 2008/0001919 A1 | 1/2008 | Pascucci |
| 2008/0004633 A1 | 1/2008 | Arata et al. |
| 2008/0015664 A1 | 1/2008 | Podhajsky |
| 2008/0069433 A1 | 3/2008 | Corcoran et al. |
| 2008/0077158 A1 | 3/2008 | Haider et al. |
| 2008/0144906 A1 | 6/2008 | Allred et al. |
| 2008/0151233 A1 | 6/2008 | Blanke et al. |
| 2008/0194930 A1 | 8/2008 | Harris et al. |
| 2008/0205588 A1 | 8/2008 | Kim |
| 2008/0228104 A1 | 9/2008 | Uber et al. |
| 2008/0234866 A1 | 9/2008 | Kishi et al. |
| 2008/0269596 A1 | 10/2008 | Revie et al. |
| 2008/0297360 A1 | 12/2008 | Knox et al. |
| 2008/0319491 A1 | 12/2008 | Schoenefeld |
| 2009/0000627 A1 | 1/2009 | Quaid et al. |
| 2009/0012533 A1 | 1/2009 | Barbagli et al. |
| 2009/0234223 A1 | 9/2009 | Onoda et al. |
| 2009/0326336 A1 | 12/2009 | Lemke et al. |
| 2010/0030231 A1 | 2/2010 | Revie et al. |
| 2010/0036374 A1 | 2/2010 | Ward |
| 2010/0081875 A1 | 4/2010 | Fowler et al. |
| 2010/0087755 A1 | 4/2010 | Boezaart |
| 2010/0137882 A1 | 6/2010 | Quaid, III |
| 2010/0152539 A1 | 6/2010 | Ghabrial et al. |
| 2010/0194574 A1 | 8/2010 | Monk et al. |
| 2010/0217278 A1 | 8/2010 | Tripathi |
| 2010/0280493 A1 | 11/2010 | Nayak |
| 2011/0014181 A1 | 1/2011 | Thornton |
| 2011/0046476 A1 | 2/2011 | Cinquin et al. |
| 2011/0071531 A1 | 3/2011 | Carson |
| 2011/0082369 A1 | 4/2011 | Mohr et al. |
| 2011/0201881 A1 | 8/2011 | Emch |
| 2011/0257611 A1 | 10/2011 | Locke et al. |
| 2011/0257661 A1 | 10/2011 | Choi et al. |
| 2011/0306985 A1 | 12/2011 | Inoue et al. |
| 2012/0004894 A1 | 1/2012 | Butler et al. |
| 2012/0046668 A1 | 2/2012 | Gantes |
| 2012/0143341 A1 | 6/2012 | Zipnick |
| 2012/0165837 A1 | 6/2012 | Belman et al. |
| 2012/0265022 A1 | 10/2012 | Menn |
| 2012/0300051 A1 | 11/2012 | Daigo et al. |
| 2013/0035583 A1 | 2/2013 | Park et al. |
| 2013/0053679 A1 | 2/2013 | Owen |
| 2013/0090554 A1 | 4/2013 | Zvuloni et al. |
| 2013/0100250 A1 | 4/2013 | Raskar et al. |
| 2013/0172902 A1 | 7/2013 | Lightcap et al. |
| 2013/0211244 A1 | 8/2013 | Nathaniel |
| 2013/0274596 A1 | 10/2013 | Azizian et al. |
| 2013/0274673 A1 | 10/2013 | Fischell et al. |
| 2013/0274674 A1 | 10/2013 | Fischell et al. |
| 2013/0296712 A1 | 11/2013 | Durvasula |
| 2014/0005685 A1 | 1/2014 | Modrow et al. |
| 2014/0024945 A1 | 1/2014 | Mung et al. |
| 2014/0035762 A1 | 2/2014 | Shelton, IV et al. |
| 2014/0039520 A1 | 2/2014 | Haider et al. |
| 2014/0114180 A1 | 4/2014 | Jain |
| 2014/0148679 A1 | 5/2014 | Eary et al. |
| 2014/0163359 A1 | 6/2014 | Sholev et al. |
| 2014/0163664 A1 | 6/2014 | Goldsmith |
| 2014/0171793 A1 | 6/2014 | Lin et al. |
| 2014/0175150 A1 | 6/2014 | Shelton, IV et al. |
| 2014/0179997 A1 | 6/2014 | von Grunberg et al. |
| 2014/0267549 A1 | 9/2014 | Pinter et al. |
| 2014/0320684 A1 | 10/2014 | Chatenever et al. |
| 2014/0336461 A1 | 11/2014 | Reiter et al. |
| 2014/0378843 A1 | 12/2014 | Valdes et al. |
| 2015/0009473 A1 | 1/2015 | Su |
| 2015/0018999 A1 | 1/2015 | Lee et al. |
| 2015/0025548 A1 | 1/2015 | Franklin et al. |
| 2015/0032140 A1 | 1/2015 | Khouri |
| 2015/0051460 A1 | 2/2015 | Saxena et al. |
| 2015/0066107 A1 | 3/2015 | Richter et al. |
| 2015/0133909 A1* | 5/2015 | van der Weide ...... A61B 90/37 606/33 |
| 2015/0145966 A1 | 5/2015 | Krieger et al. |
| 2015/0202005 A1 | 7/2015 | Fuflyigin et al. |
| 2015/0209035 A1 | 7/2015 | Zemlok |
| 2015/0223903 A1 | 8/2015 | Bell et al. |
| 2015/0238071 A1 | 8/2015 | Hua et al. |
| 2015/0238276 A1 | 8/2015 | Atarot et al. |
| 2015/0243056 A1 | 8/2015 | Lee et al. |
| 2015/0245878 A1 | 9/2015 | Jaramaz et al. |
| 2015/0272557 A1 | 10/2015 | Overmyer et al. |
| 2015/0297177 A1 | 10/2015 | Boctor et al. |
| 2015/0305650 A1 | 10/2015 | Hunter et al. |
| 2015/0366628 A1 | 12/2015 | Ingmanson |
| 2015/0374435 A1 | 12/2015 | Cao et al. |
| 2016/0000516 A1 | 1/2016 | Cheng et al. |
| 2016/0007827 A1 | 1/2016 | Frimer et al. |
| 2016/0014328 A1 | 1/2016 | Rokutanda |
| 2016/0022146 A1 | 1/2016 | Piron et al. |
| 2016/0038004 A1 | 2/2016 | Tanaka |
| 2016/0070436 A1 | 3/2016 | Thomas et al. |
| 2016/0086380 A1 | 3/2016 | Vayser et al. |
| 2016/0135909 A1 | 5/2016 | Ogawa et al. |
| 2016/0183841 A1 | 6/2016 | Duindam et al. |
| 2016/0206204 A1 | 7/2016 | Matsuda et al. |
| 2016/0228090 A1 | 8/2016 | Boctor et al. |
| 2016/0235304 A1 | 8/2016 | Tzoumas et al. |
| 2016/0256101 A1 | 9/2016 | Aharoni et al. |
| 2016/0270861 A1 | 9/2016 | Guru et al. |
| 2016/0331467 A1 | 11/2016 | Slamin et al. |
| 2016/0338795 A1* | 11/2016 | Vayser ................... G02B 27/48 |
| 2016/0346034 A1 | 12/2016 | Arya et al. |
| 2017/0007350 A1 | 1/2017 | Popovic et al. |
| 2017/0020460 A1 | 1/2017 | Leblond et al. |
| 2017/0020613 A1 | 1/2017 | Kang et al. |
| 2017/0055819 A1 | 3/2017 | Hansen et al. |
| 2017/0059408 A1 | 3/2017 | Korner et al. |
| 2017/0071475 A1 | 3/2017 | Irisawa |
| 2017/0071688 A1 | 3/2017 | Cohen et al. |
| 2017/0079530 A1 | 3/2017 | DiMaio et al. |
| 2017/0099479 A1 | 4/2017 | Browd et al. |
| 2017/0165008 A1 | 6/2017 | Finley |
| 2017/0172382 A1 | 6/2017 | Nir et al. |
| 2017/0172662 A1 | 6/2017 | Panescu et al. |
| 2017/0180704 A1 | 6/2017 | Panescu et al. |
| 2017/0181808 A1 | 6/2017 | Panescu et al. |
| 2017/0181809 A1 | 6/2017 | Panescu et al. |
| 2017/0189006 A1 | 7/2017 | Shluzas et al. |
| 2017/0197028 A1 | 7/2017 | Goldsmith |
| 2017/0202624 A1 | 7/2017 | Atarot et al. |
| 2017/0238962 A1 | 8/2017 | Hansen et al. |
| 2017/0251900 A1 | 9/2017 | Hansen et al. |
| 2017/0258526 A1 | 9/2017 | Lang |
| 2017/0265943 A1 | 9/2017 | Sela et al. |
| 2017/0265947 A1 | 9/2017 | Dyer et al. |
| 2017/0296213 A1 | 10/2017 | Swensgard et al. |
| 2017/0304007 A1* | 10/2017 | Piron ..................... A61B 34/20 |
| 2017/0312032 A1 | 11/2017 | Amanatullah et al. |
| 2017/0319057 A1 | 11/2017 | Inglese et al. |
| 2017/0366773 A1 | 12/2017 | Kiraly et al. |
| 2017/0367580 A1 | 12/2017 | DiMaio et al. |
| 2018/0000533 A1 | 1/2018 | Boll et al. |
| 2018/0014777 A1 | 1/2018 | Amir et al. |
| 2018/0014851 A1 | 1/2018 | Hansen et al. |
| 2018/0064498 A1 | 3/2018 | Kapadia et al. |
| 2018/0082480 A1 | 3/2018 | White et al. |
| 2018/0168741 A1 | 6/2018 | Swayze et al. |
| 2018/0214016 A1 | 8/2018 | Thommen et al. |
| 2018/0228555 A1 | 8/2018 | Charron et al. |
| 2018/0228559 A1 | 8/2018 | Brierton et al. |
| 2018/0235715 A1 | 8/2018 | Amiot et al. |
| 2018/0242967 A1 | 8/2018 | Meade |

(56) References Cited

U.S. PATENT DOCUMENTS

| | | |
|---|---|---|
| 2018/0247128 A1 | 8/2018 | Alvi et al. |
| 2018/0247153 A1* | 8/2018 | Ganapati ................ G06N 3/08 |
| 2018/0250086 A1 | 9/2018 | Grubbs |
| 2018/0271603 A1 | 9/2018 | Nir et al. |
| 2018/0271615 A1 | 9/2018 | Mahadik et al. |
| 2018/0333210 A1 | 11/2018 | Nijkamp et al. |
| 2018/0338806 A1 | 11/2018 | Grubbs |
| 2018/0343381 A1 | 11/2018 | Kobayashi et al. |
| 2018/0344140 A1 | 12/2018 | Aizenfeld |
| 2018/0368883 A1 | 12/2018 | Rossa et al. |
| 2019/0000478 A1 | 1/2019 | Messerly et al. |
| 2019/0008579 A1 | 1/2019 | Begg et al. |
| 2019/0022418 A1 | 1/2019 | Fishman |
| 2019/0046276 A1 | 2/2019 | Inglese et al. |
| 2019/0053691 A1 | 2/2019 | Hansen et al. |
| 2019/0053872 A1 | 2/2019 | Meglan |
| 2019/0059736 A1 | 2/2019 | Maier-Hein et al. |
| 2019/0069824 A1 | 3/2019 | Darty et al. |
| 2019/0076186 A1 | 3/2019 | Fischell et al. |
| 2019/0099070 A1 | 4/2019 | Mark et al. |
| 2019/0099226 A1 | 4/2019 | Hallen |
| 2019/0104919 A1 | 4/2019 | Shelton, IV et al. |
| 2019/0110924 A1 | 4/2019 | Moreno et al. |
| 2019/0117319 A1 | 4/2019 | Cima et al. |
| 2019/0125361 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125459 A1 | 5/2019 | Shelton, IV et al. |
| 2019/0142524 A1 | 5/2019 | Hladio et al. |
| 2019/0159848 A1 | 5/2019 | Quaid et al. |
| 2019/0172371 A1 | 6/2019 | Eckert et al. |
| 2019/0175272 A1 | 6/2019 | Khan et al. |
| 2019/0180865 A1 | 6/2019 | Kashima et al. |
| 2019/0192145 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200998 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201102 A1 | 7/2019 | Shelton, IV et al. |
| 2019/0201111 A1 | 7/2019 | Shelton, IV et al. |
| 2019/0201116 A1 | 7/2019 | Shelton, IV et al. |
| 2019/0201120 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205567 A1 | 7/2019 | Shelton, IV et al. |
| 2019/0206050 A1 | 7/2019 | Yates et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0208641 A1 | 7/2019 | Yates et al. |
| 2019/0223961 A1 | 7/2019 | Barral et al. |
| 2019/0247050 A1 | 8/2019 | Goldsmith |
| 2019/0269476 A1 | 9/2019 | Bowling et al. |
| 2019/0279524 A1 | 9/2019 | Stoyanov et al. |
| 2019/0290524 A1 | 9/2019 | Augustine et al. |
| 2019/0293554 A1 | 9/2019 | Nakao et al. |
| 2019/0307524 A1 | 10/2019 | Popovic |
| 2019/0311542 A1 | 10/2019 | Douglas et al. |
| 2019/0320117 A1 | 10/2019 | Wu et al. |
| 2019/0320878 A1 | 10/2019 | Duindam et al. |
| 2019/0321118 A1 | 10/2019 | Genova et al. |
| 2019/0374140 A1 | 12/2019 | Tucker et al. |
| 2019/0388157 A1 | 12/2019 | Shameli et al. |
| 2020/0008879 A1 | 1/2020 | Popovic et al. |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015904 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0018844 A1 | 1/2020 | Fridman et al. |
| 2020/0030036 A1 | 1/2020 | Forstein |
| 2020/0037858 A1 | 2/2020 | Pedreira de Cerqueira Filho |
| 2020/0038112 A1 | 2/2020 | Amanatullah et al. |
| 2020/0060725 A1 | 2/2020 | Sato |
| 2020/0078120 A1 | 3/2020 | Aldridge et al. |
| 2020/0121245 A1 | 4/2020 | Barclay et al. |
| 2020/0188032 A1 | 6/2020 | Komp et al. |
| 2020/0222146 A1 | 7/2020 | Komp |
| 2020/0246073 A1 | 8/2020 | Rossetto et al. |
| 2020/0253669 A1 | 8/2020 | Diolaiti et al. |
| 2020/0271565 A1 | 8/2020 | Gütle et al. |
| 2020/0273577 A1 | 8/2020 | Wolf et al. |
| 2020/0281662 A1 | 9/2020 | Cong et al. |
| 2020/0289205 A1 | 9/2020 | Scheib et al. |
| 2020/0289216 A1 | 9/2020 | Denlinger et al. |
| 2020/0289217 A1 | 9/2020 | Denlinger et al. |
| 2020/0289219 A1 | 9/2020 | Denlinger et al. |
| 2020/0289220 A1 | 9/2020 | Denlinger et al. |
| 2020/0289221 A1 | 9/2020 | Denlinger et al. |
| 2020/0289222 A1 | 9/2020 | Denlinger et al. |
| 2020/0289223 A1 | 9/2020 | Denlinger et al. |
| 2020/0289228 A1 | 9/2020 | Denlinger et al. |
| 2020/0289229 A1 | 9/2020 | Denlinger et al. |
| 2020/0289230 A1 | 9/2020 | Denlinger et al. |
| 2020/0291476 A1 | 9/2020 | Deng et al. |
| 2020/0315721 A1 | 10/2020 | Rabindran et al. |
| 2020/0330166 A1 | 10/2020 | Meglan et al. |
| 2020/0345451 A1 | 11/2020 | Peine et al. |
| 2020/0367972 A1 | 11/2020 | Zhang et al. |
| 2020/0397266 A1 | 12/2020 | Hufford |
| 2020/0405395 A1 | 12/2020 | Gullotti et al. |
| 2021/0045838 A1 | 2/2021 | Bradbury et al. |
| 2021/0068908 A1 | 3/2021 | Thienphrapa et al. |
| 2021/0137634 A1 | 5/2021 | Lang |
| 2021/0153943 A1 | 5/2021 | Piron et al. |
| 2021/0196098 A1 | 7/2021 | Shelton, IV et al. |
| 2021/0196108 A1 | 7/2021 | Shelton, IV |
| 2021/0196109 A1 | 7/2021 | Shelton, IV et al. |
| 2021/0196381 A1 | 7/2021 | Eckert et al. |
| 2021/0196382 A1 | 7/2021 | Mumaw et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196423 A1 | 7/2021 | Shelton, IV et al. |
| 2021/0196424 A1 | 7/2021 | Shelton, IV et al. |
| 2021/0196425 A1 | 7/2021 | Shelton, IV et al. |
| 2021/0199557 A1 | 7/2021 | Shelton, IV et al. |
| 2021/0205019 A1 | 7/2021 | Shelton, IV et al. |
| 2021/0212792 A1 | 7/2021 | Shelton, IV et al. |
| 2021/0212794 A1 | 7/2021 | Shelton, IV et al. |
| 2021/0259660 A1 | 8/2021 | Bharat et al. |
| 2021/0259789 A1 | 8/2021 | Wright et al. |
| 2021/0275251 A1 | 9/2021 | Shelton, IV et al. |
| 2021/0275252 A1 | 9/2021 | Shelton, IV et al. |
| 2021/0282861 A1 | 9/2021 | Eckert et al. |
| 2021/0307835 A1 | 10/2021 | Shelton, IV et al. |
| 2021/0307865 A1 | 10/2021 | Shelton, IV et al. |
| 2021/0307866 A1 | 10/2021 | Shelton, IV et al. |
| 2021/0307867 A1 | 10/2021 | Shelton, IV et al. |
| 2021/0307868 A1 | 10/2021 | Shelton, IV et al. |
| 2021/0307869 A1 | 10/2021 | Shelton, IV et al. |
| 2021/0307870 A1 | 10/2021 | Shelton, IV et al. |

(56) References Cited

U.S. PATENT DOCUMENTS

| | | |
|---|---|---|
| 2021/0315645 A1 | 10/2021 | Hares et al. |
| 2022/0000559 A1 | 1/2022 | Leonard et al. |
| 2022/0000565 A1 | 1/2022 | Gururaj et al. |
| 2022/0047259 A1 | 2/2022 | Prior et al. |
| 2022/0079675 A1 | 3/2022 | Lang |
| 2022/0133412 A1 | 5/2022 | Tolkowsky et al. |
| 2022/0273288 A1 | 9/2022 | Scheib et al. |
| 2022/0323066 A1 | 10/2022 | Scheib et al. |
| 2023/0046220 A1 | 2/2023 | Scheib et al. |
| 2023/0074951 A1 | 3/2023 | Scheib et al. |

FOREIGN PATENT DOCUMENTS

| | | |
|---|---|---|
| EP | 2700365 A1 | 2/2014 |
| EP | 2754383 A2 | 7/2014 |
| EP | 3367387 A1 | 8/2018 |
| JP | 2006280591 A | 10/2006 |
| JP | 4106991 B2 | 6/2008 |
| KR | 20120068597 A | 6/2012 |
| WO | WO-2008033133 A2 | 3/2008 |
| WO | WO-2013093391 A1 | 6/2013 |
| WO | WO-2013163391 A1 | 10/2013 |
| WO | WO-2015135058 A1 | 9/2015 |
| WO | WO-2017042171 A1 | 3/2017 |
| WO | WO-2018171851 A1 | 9/2018 |
| WO | WO-2018200767 A1 | 11/2018 |
| WO | WO-2019130085 A1 | 7/2019 |
| WO | WO-2020116991 A1 | 6/2020 |

OTHER PUBLICATIONS

Thyroid Fine Needle Aspiration (FNA) Biopsy, retrieved from www.fairview.org/patient-education/90246 on Feb. 4, 2020. 3 pages.

Open Technique for Low Anterior Resection, retrieved from https://abdominalkey.com/open-technique-for-low-anterior-resection/ on Feb. 4, 2020. 6 pages.

Sukumar et al., "Robotic Partial Nephrectomy Using Robotic Bulldog Clamps," JSLS: Journal of the Society of Laparoendoscopic Surgeons, 15(4), pp. 520-526, 2011.

X12C4 Robotic Drop-In, retrieved from https://bkultrasound.com/transducers/x12c4-robotic-drop-in on Feb. 13, 2020. 2 pages.

"ATM-MPLS Networking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.

Elhaj, et al., "Sleeve Gastrectomy Surgical Assistive Instrument for Accurate Remnant Stomach Volume," ASME, J. Med. Devices, vol. 4, pp. 1-10, Jun. 2010.

Brecht, Hans-Peter et al., "Whole-body three-dimensional optoacoustic tomography system for small animals," Journal of Biomedical Optics, vol. 14, No. 6, 064007-1-064007-7 (2009).

Ge, Jiawei et al., "Landmark-Guided Deformable Image Registration for Supervised Autonomous Robotic Tumor Resection," Advances in Intelligent Data Analysis XIX, LNCS, Springer International Publishing, pp. 320-328, Oct. 10, 2019.

Ueda et al., "Quantitative computed tomography for the prediction of pulmonary function after lung cancer surgery: a simple method using simulation software," European Journal of Cardio-thoracic Surgery, 35 (2009) 414-418.

Fuchs et al., "Three-dimensional visualization and virtual simulation of resections in pediatric solid tumors," Journal of Pediatric Surgery (2005) 40, 364-370.

Brainlab Ag: "iPLAN Cranial—Software user guide", Jan. 1, 2014, Retrieved from the internet: URL: https://userguides.brainlab.com/wp-content/uploads/2019/12/iPlan-Cranial-3.0-Software-User-Guide-English-60914-63EN-Rev.1.4.pdf, pp. 1-268 (Jan. 1, 2014).

* cited by examiner

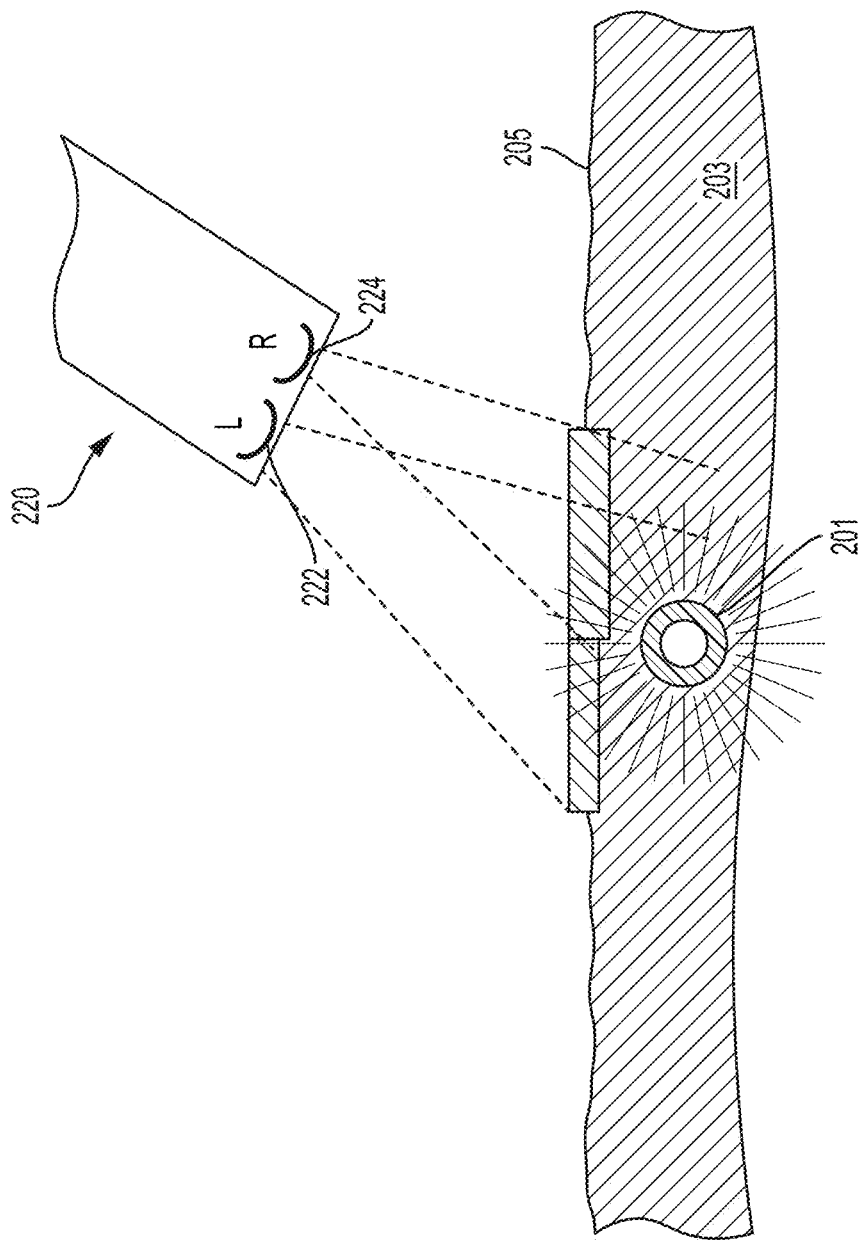

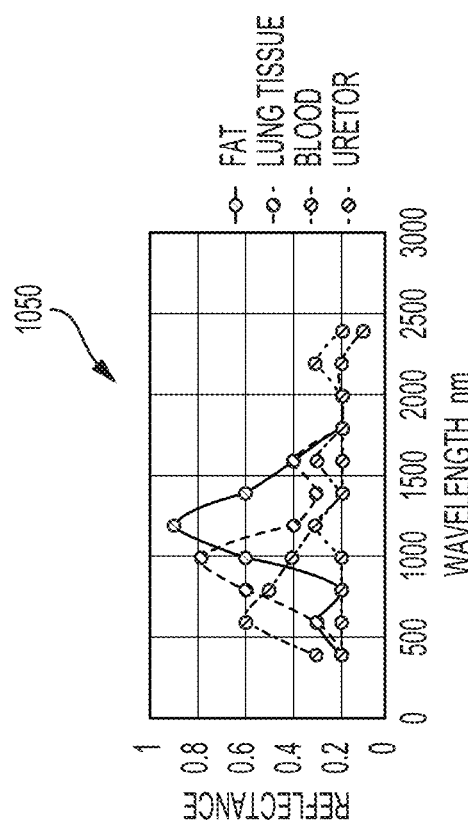
FIG. 16
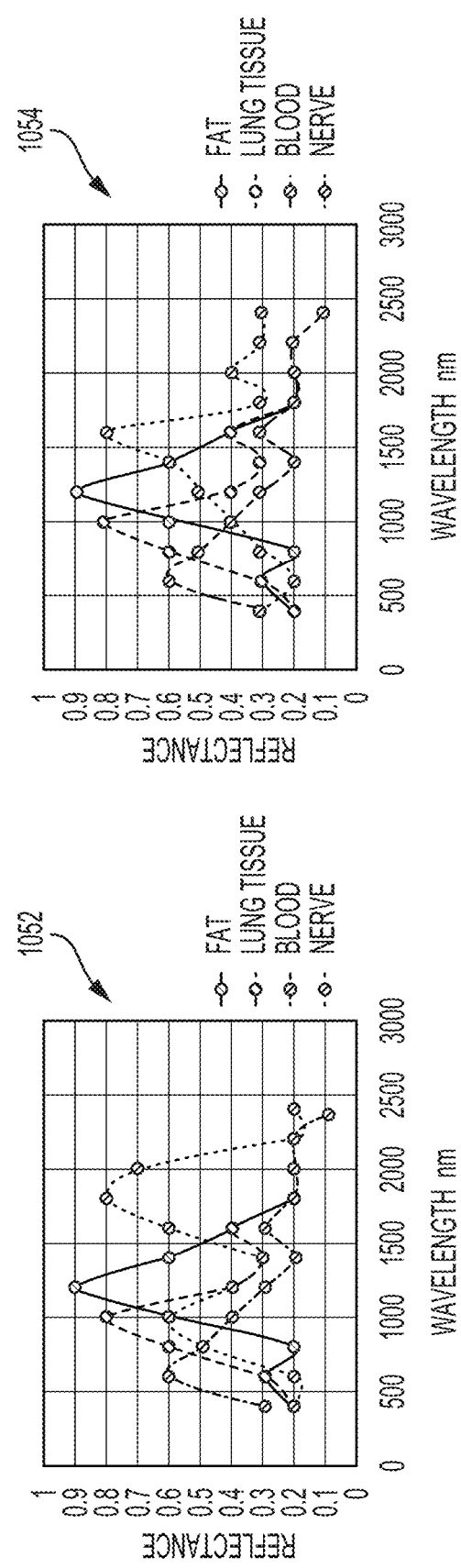
FIG. 17
FIG. 18

CONTROLLING AN EMITTER ASSEMBLY PULSE SEQUENCE

CROSS-REFERENCE TO RELATED APPLICATION

The present application claims priority under 35 U.S.C. § 119(e) to U.S. Provisional Patent Application No. 62/698,625, titled DIGITAL SURGERY IMAGING/VISUALIZATION SYSTEM, filed Jul. 16, 2018, the disclosure of which is hereby incorporated by reference in its entirety.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

In one general aspect, a surgical instrument for visualizing a surgical site. The surgical instrument comprises an emitter assembly configured to emit electromagnetic radiation at the surgical site, the electromagnetic radiation comprising at least one of infrared radiation, visible light, or structured light; a receiver assembly configured to receive the electromagnetic radiation reflected from the surgical site; and a control circuit coupled to the emitter assembly and the receiver assembly. The control circuit is configured to: cause the emitter assembly to pulse the electromagnetic radiation in a sequence comprising at least one of the infrared radiation, the visible light, or the structured light; detect reflected electromagnetic radiation corresponding to the emitted electromagnetic radiation via the receiver assembly; determine tissue information according to the reflected electromagnetic radiation; and modify the sequence at which at least one of the infrared radiation, the visible light, or the structured light is emitted by the emitter assembly according to the tissue information.

In another general aspect, a surgical visualization system for visualizing a surgical site. The surgical visualization system comprises a control circuit configured to: cause electromagnetic radiation to be pulsed in a sequence comprising at least one of the infrared radiation, the visible light, or the structured light; extract tissue information from reflected electromagnetic radiation corresponding to the emitted electromagnetic radiation; and modify the sequence at which at least one of the infrared radiation, the visible light, or the structured light is emitted according to the tissue information.

In yet another general aspect, a surgical instrument for visualizing a surgical site. The surgical instrument comprises an emitter assembly configured to emit electromagnetic radiation at the surgical site, the electromagnetic radiation comprising at least one of infrared radiation, visible light, or structured light; a receiver assembly configured to receive the electromagnetic radiation reflected from the surgical site; and a control circuit coupled to the emitter assembly and the receiver assembly. The control circuit is configured to: receive a tissue type selection; cause the emitter assembly to pulse the electromagnetic radiation in a sequence corresponding to the tissue type selection, the sequence comprising at least one of the infrared radiation, the visible light, or the structured light; detect reflected electromagnetic radiation corresponding to the emitted electromagnetic radiation via the receiver assembly; and determine tissue information according to the reflected electromagnetic radiation.

FIGURES

The novel features of the various aspects are set forth with particularity in the appended claims. The described aspects, however, both as to organization and methods of operation, may be best understood by reference to the following description, taken in conjunction with the accompanying drawings in which:

FIG. 6 is a schematic of a surgical visualization system including a three-dimensional camera, wherein the surgical visualization system is configured to identify a critical structure that is embedded within tissue, according to at least one aspect of the present disclosure.

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

Figure 15C:
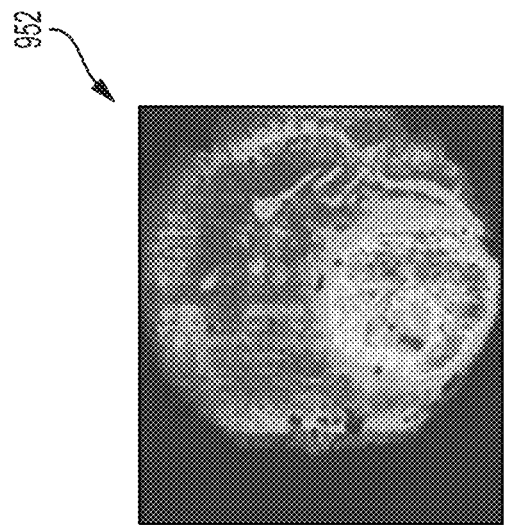
Figure 15B:
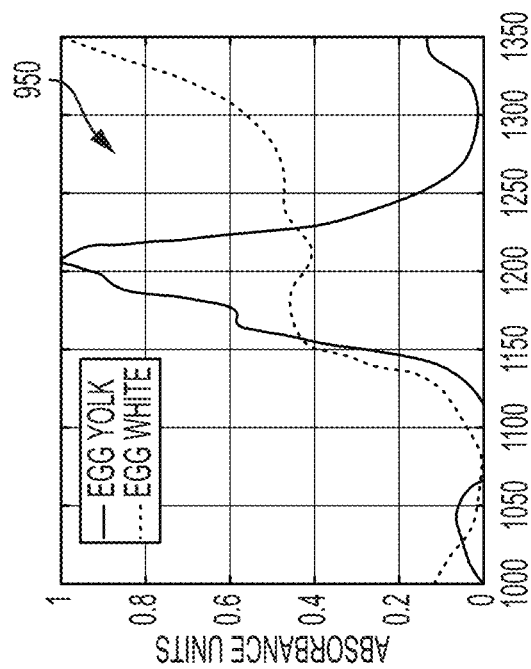
Figure 15A:
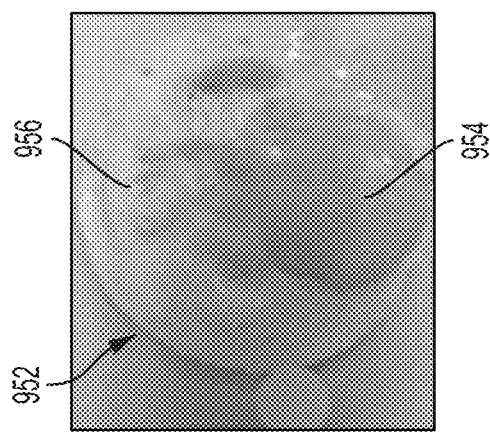

FIGS. 15A-15C show an example of a hyperspectral visualization system for imaging a fried egg, wherein FIG. 15A is a photograph of the fried egg, FIG. 15B is a graphical representation of hyperspectral signatures for an egg yolk portion and an egg white portion of the fried egg, and FIG. 15C is a hyperspectral image (shown in black-and-white) of the fried egg, in which an augmented image differentiates between the egg yolk portion and the egg white portion based on hyperspectral signature data, according to at least one aspect of the present disclosure.

FIGS. 16-18 depict illustrative hyperspectral identifying signatures to differentiate anatomy from obscurants, wherein FIG. 16 is a graphical representation of a ureter signature versus obscurants, FIG. 17 is a graphical representation of an artery signature versus obscurants, and FIG. 18 is a graphical representation of a nerve signature versus obscurants, according to at least one aspect of the present disclosure.

Figure 19:
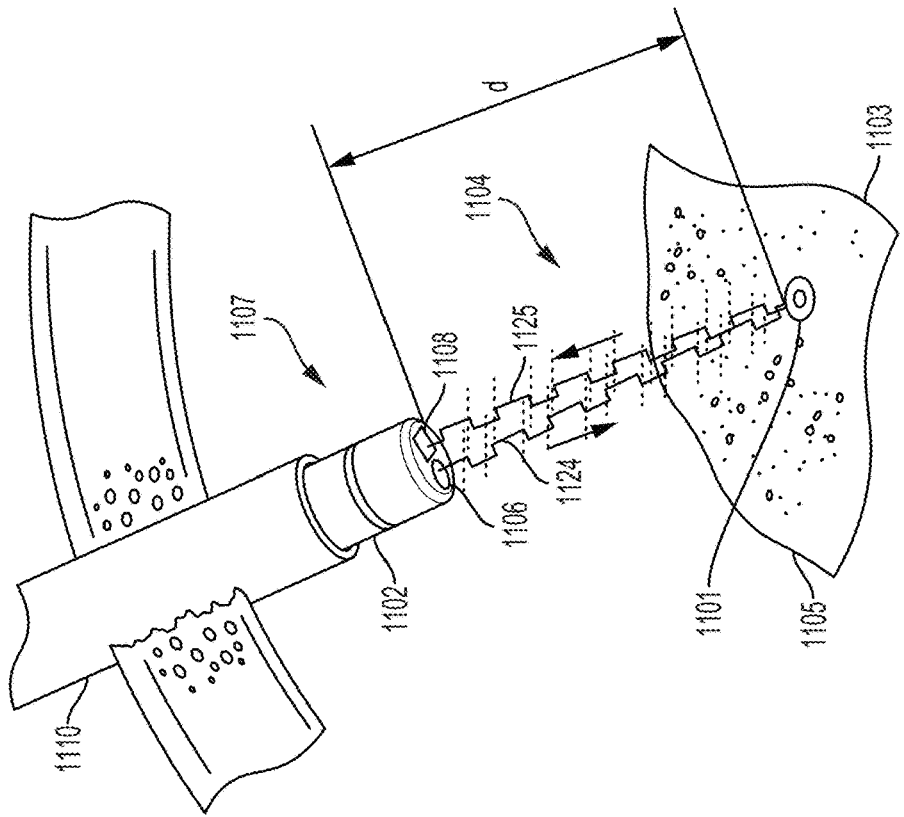

FIG. 19 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 20:
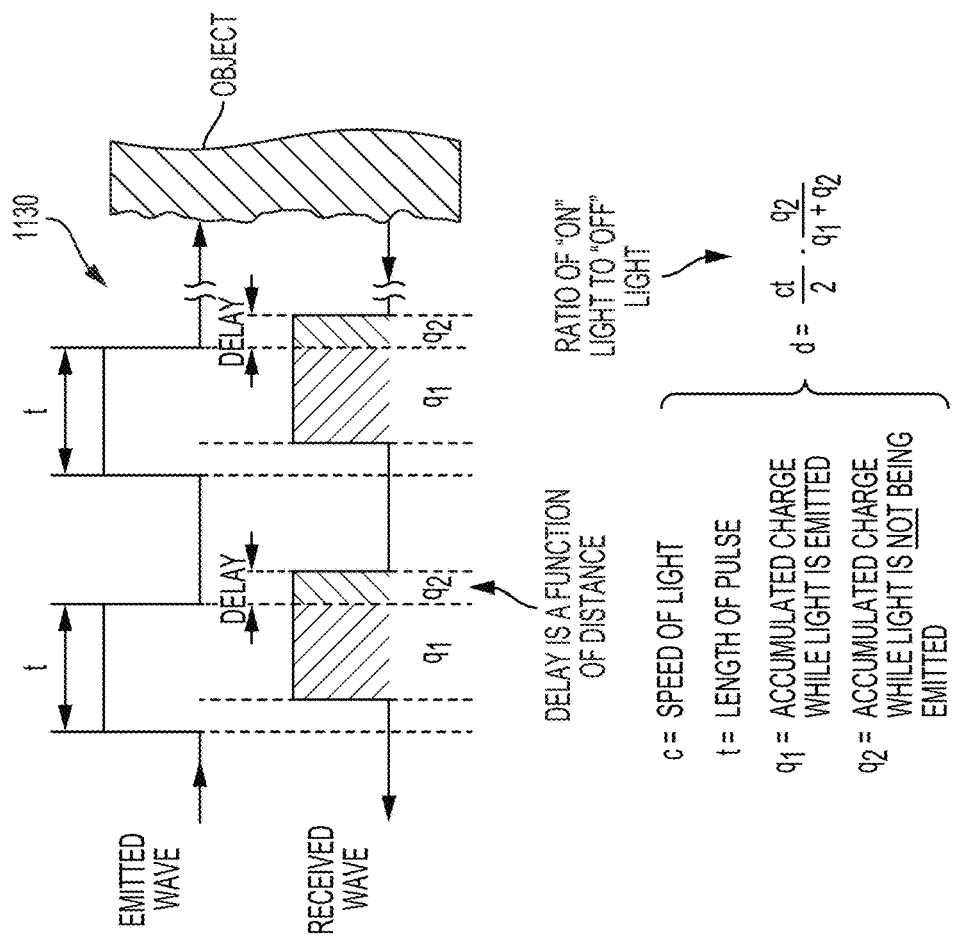

FIG. 20 is a schematic of an emitted wave, a received wave, and a delay between the emitted wave and the received wave of the NIR time-of-flight measurement system of FIG. 19, according to at least one aspect of the present disclosure.

Figure 21:
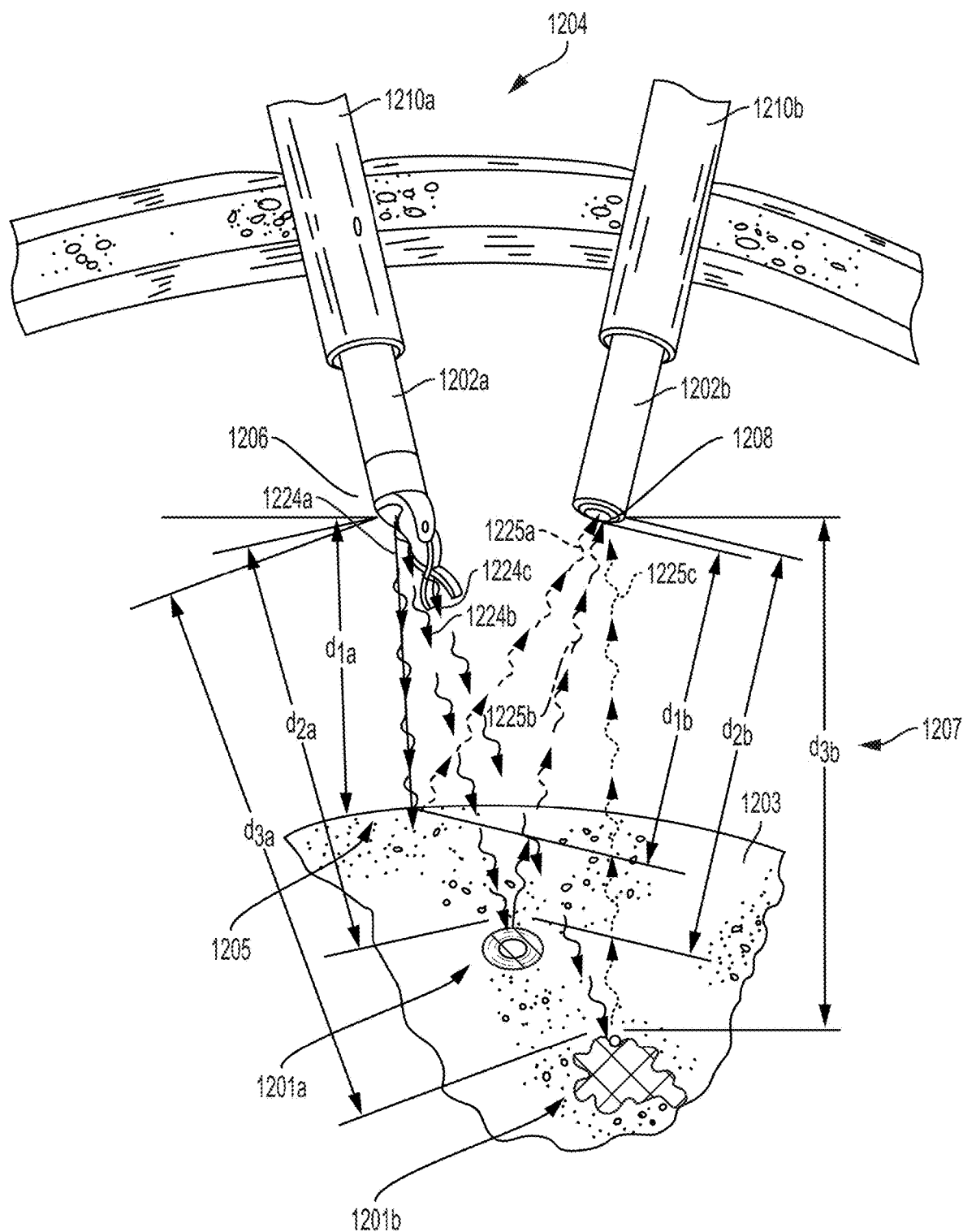

FIG. 21 illustrates a NIR time-of-flight measurement system configured to sense a distance to different structures, the time-of-flight measurement system including a transmitter (emitter) and a receiver (sensor) on separate devices, according to one aspect of the present disclosure.

Figure 22:
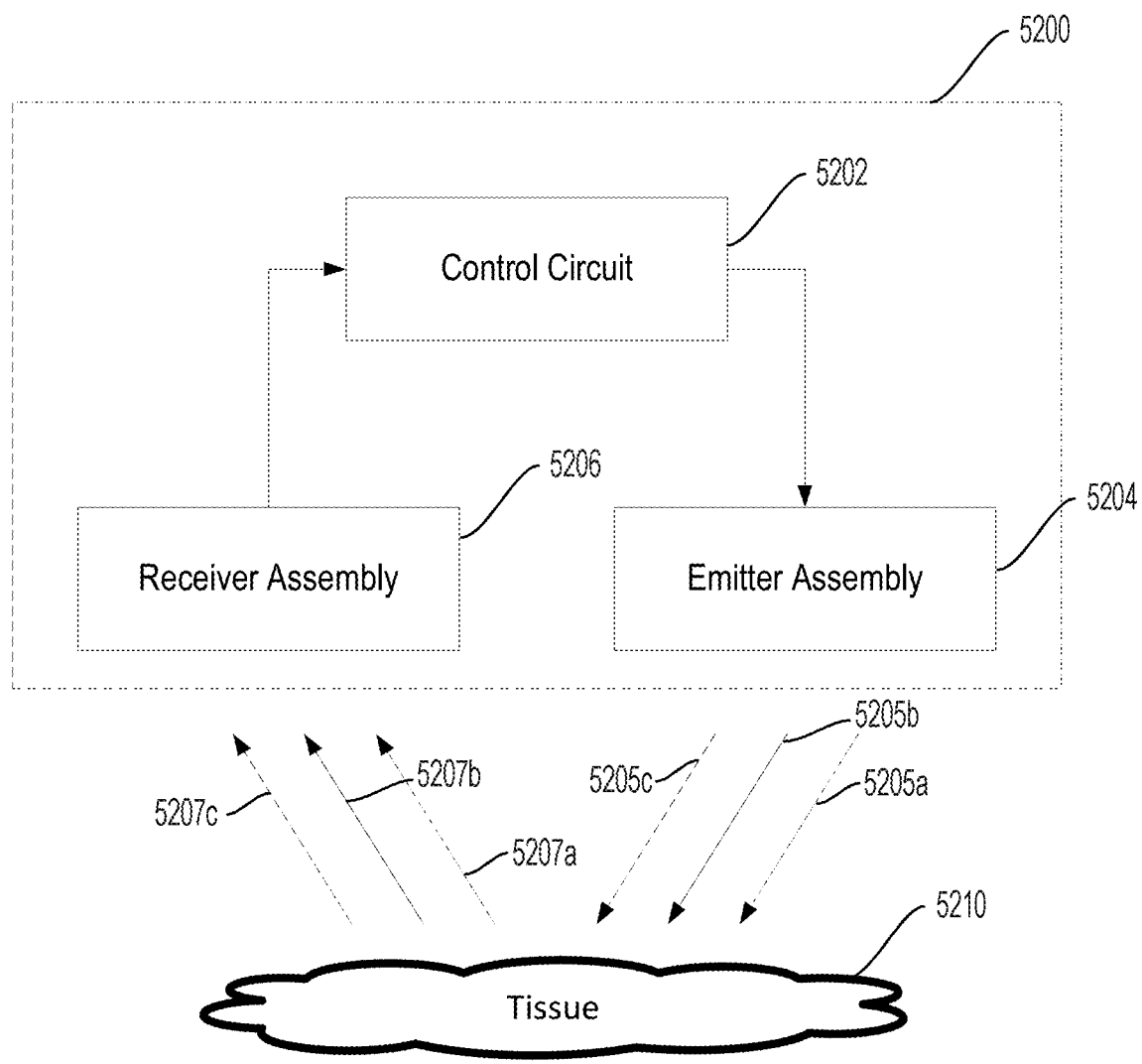

FIG. 22 illustrates a block diagram of a visualization system for intraoperative identification of structures, in accordance with at least one aspect of the present disclosure.

Figure 23:
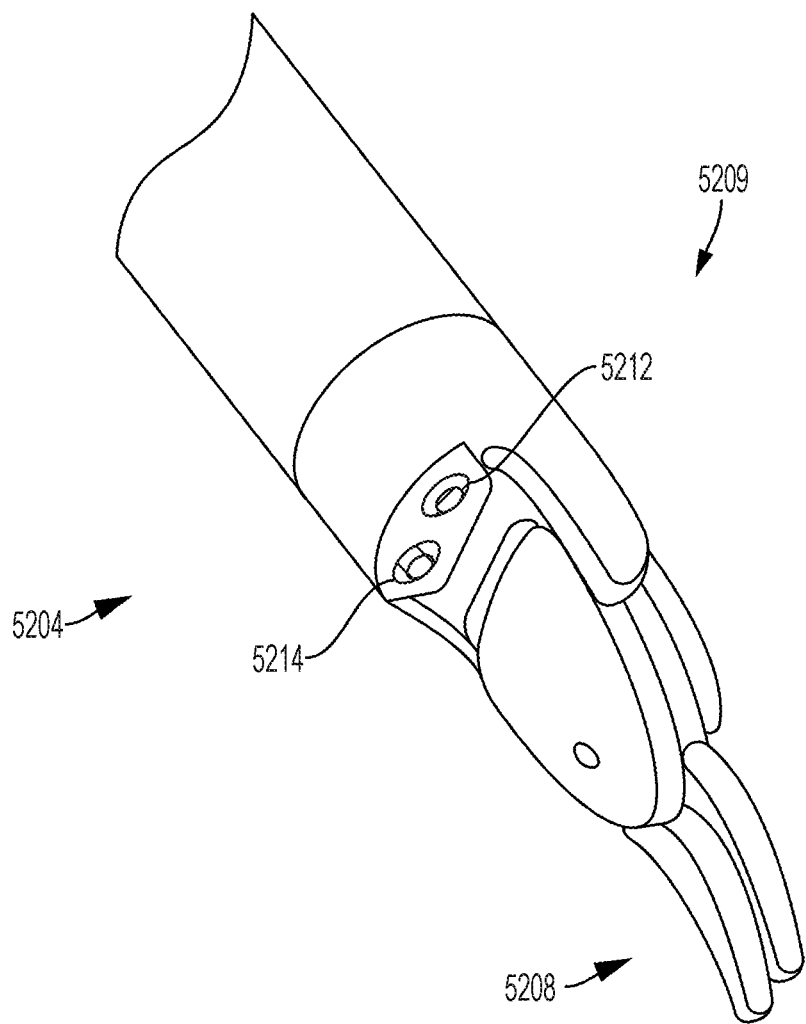

FIG. 23 illustrates a perspective view of an end effector comprising an emitter assembly, in accordance with at least one aspect of the present disclosure.

Figure 24:
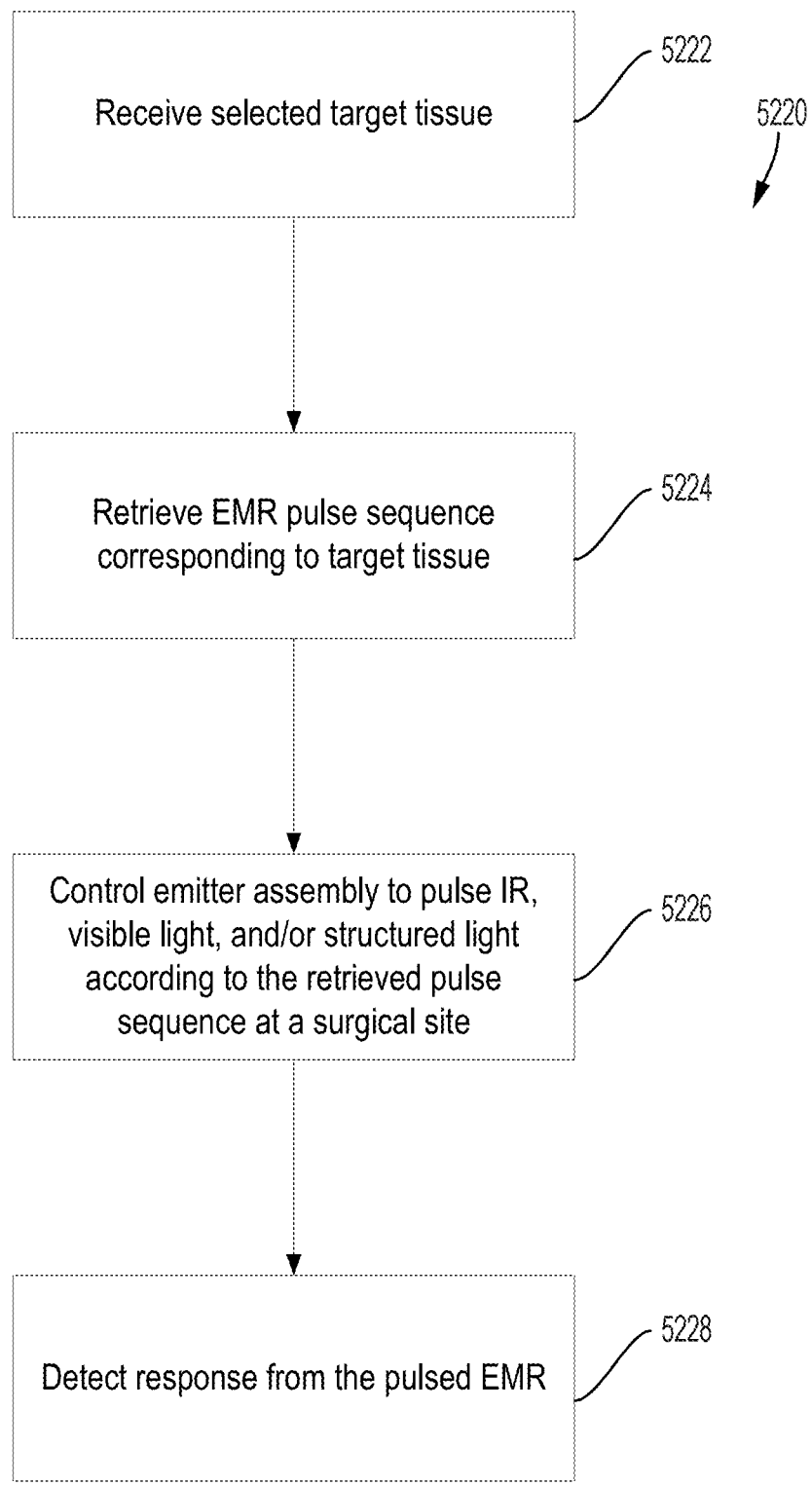

FIG. 24 illustrates a logic flow diagram of a process for visualizing tissue structures, in accordance with at least one aspect of the present disclosure.

Figure 25:
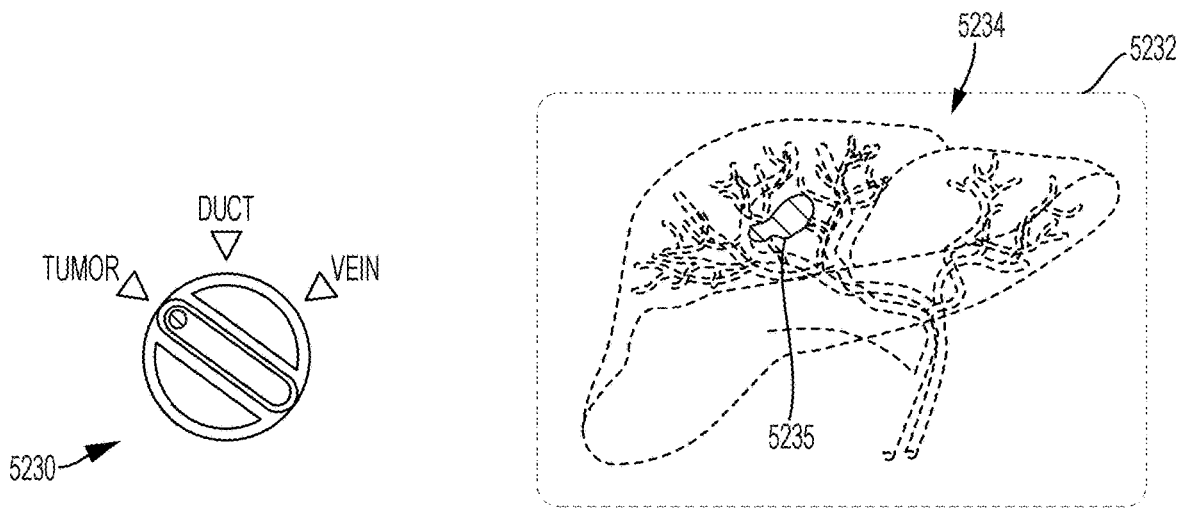

FIG. 25 illustrates a diagram of a tumor structure visualized via a visualization system, in accordance with at least one aspect of the present disclosure.

Figure 26:
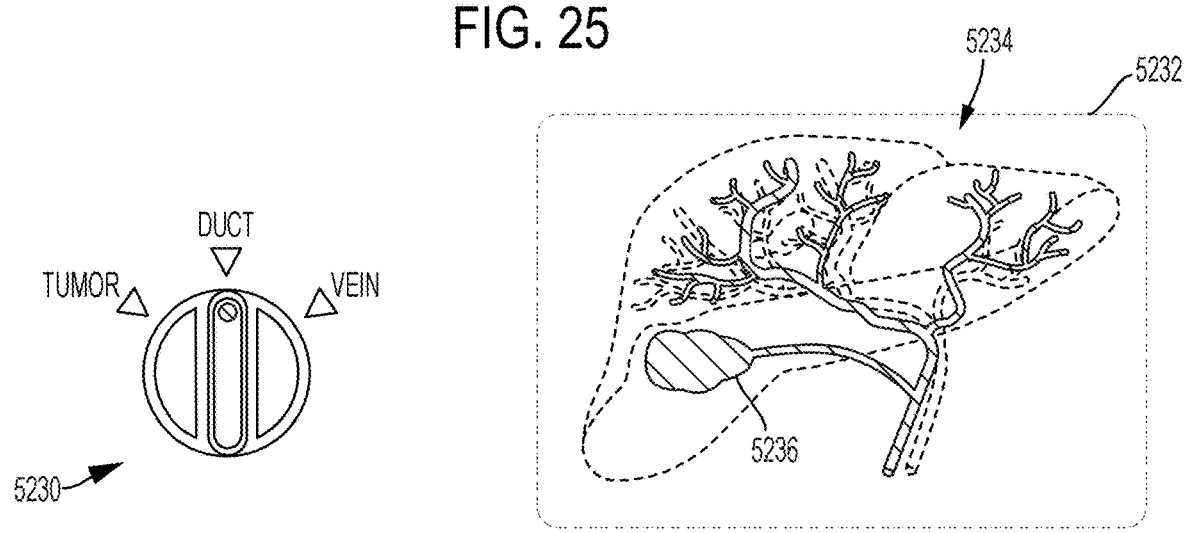

FIG. 26 illustrates a diagram of a duct structure visualized via a visualization system, in accordance with at least one aspect of the present disclosure.

Figure 27:
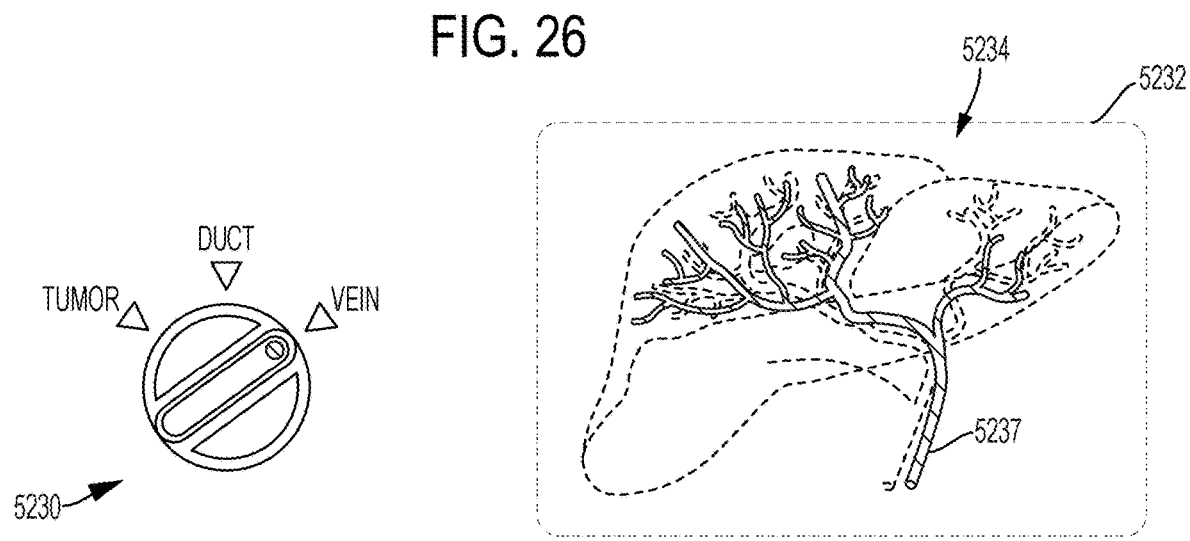

FIG. 27 illustrates a diagram of a vein structure visualized via a visualization system, in accordance with at least one aspect of the present disclosure.

Figure 28:
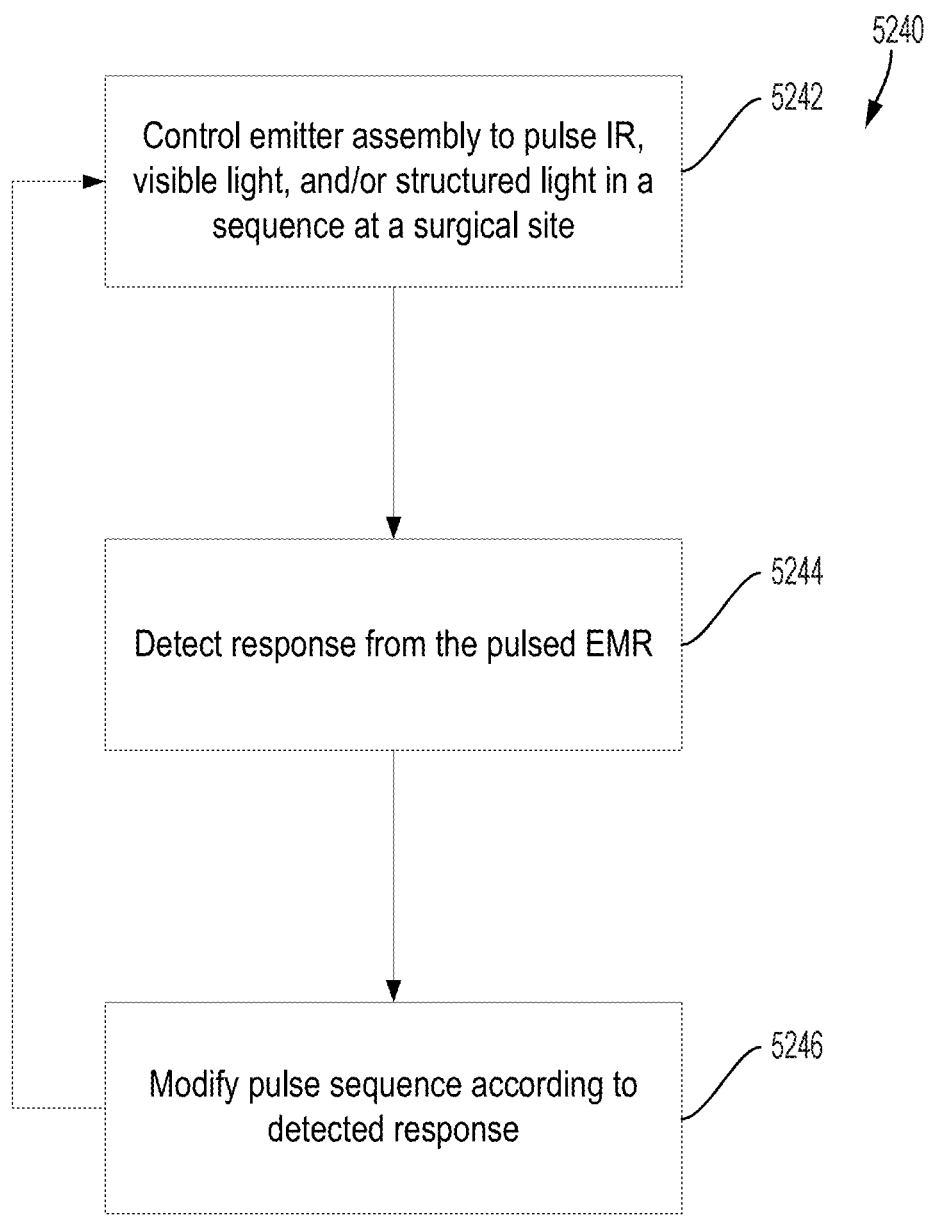

FIG. 28 illustrates a logic flow diagram of a process for automatically visualizing tissue structures, in accordance with at least one aspect of the present disclosure.

Figure 29A:
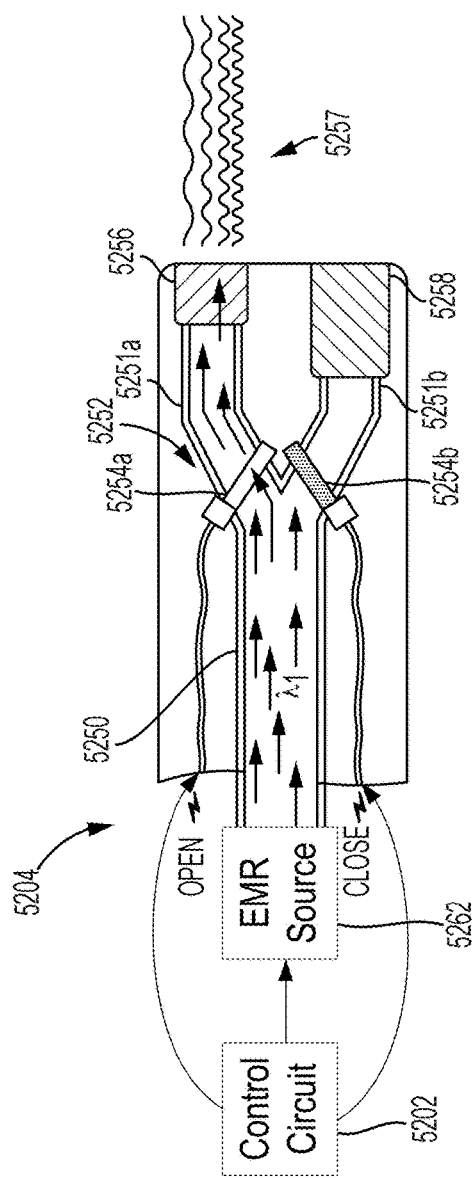

FIG. 29A illustrates a diagram of an emitter assembly including a single electromagnetic radiation (EMR) source, wherein the emitter assembly is in a first state, in accordance with at least one aspect of the present disclosure.

Figure 29B:
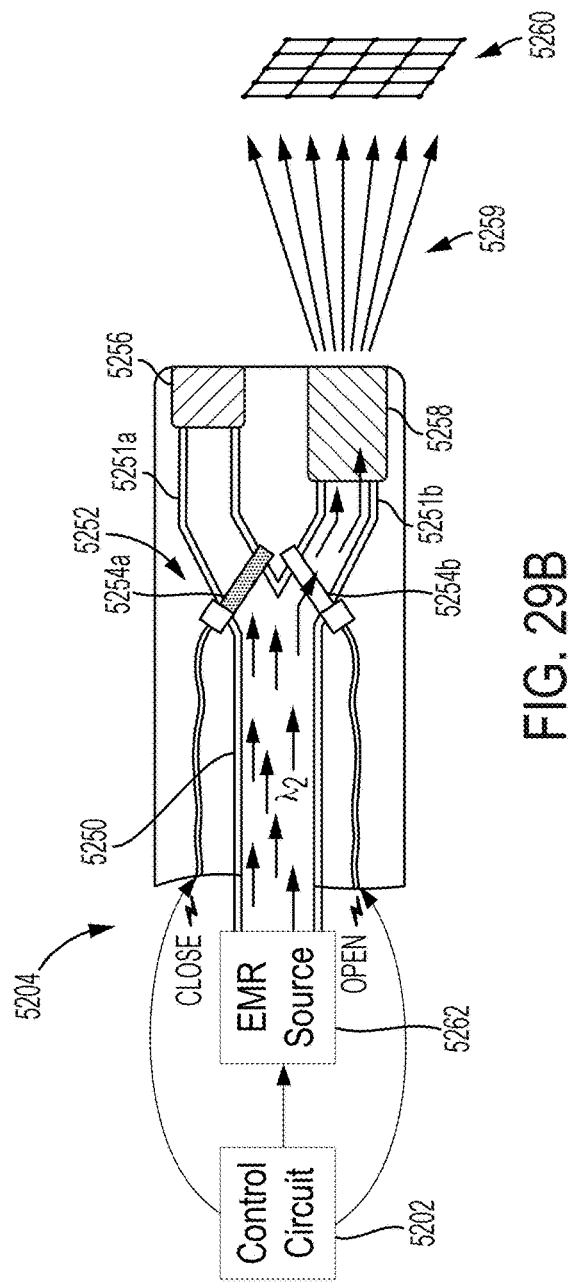

FIG. 29B illustrates a diagram of the emitter assembly of FIG. 29A, wherein the emitter assembly is in a second state, in accordance with at least one aspect of the present disclosure.

Figure 30:
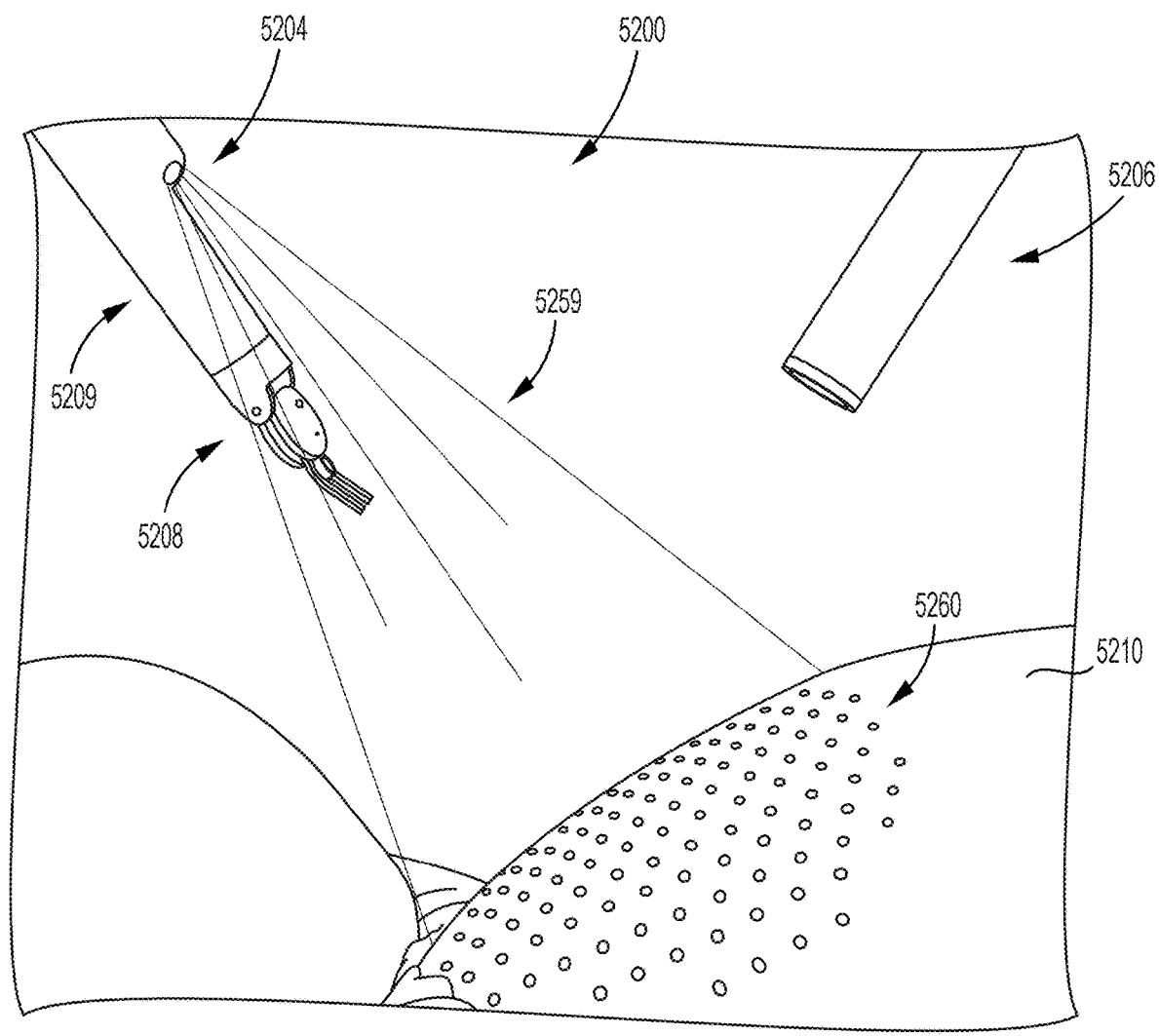

FIG. 30 illustrates a visualization system projecting structured light on a tissue at a surgical site, in accordance with at least one aspect of the present disclosure.

Figure 31A:
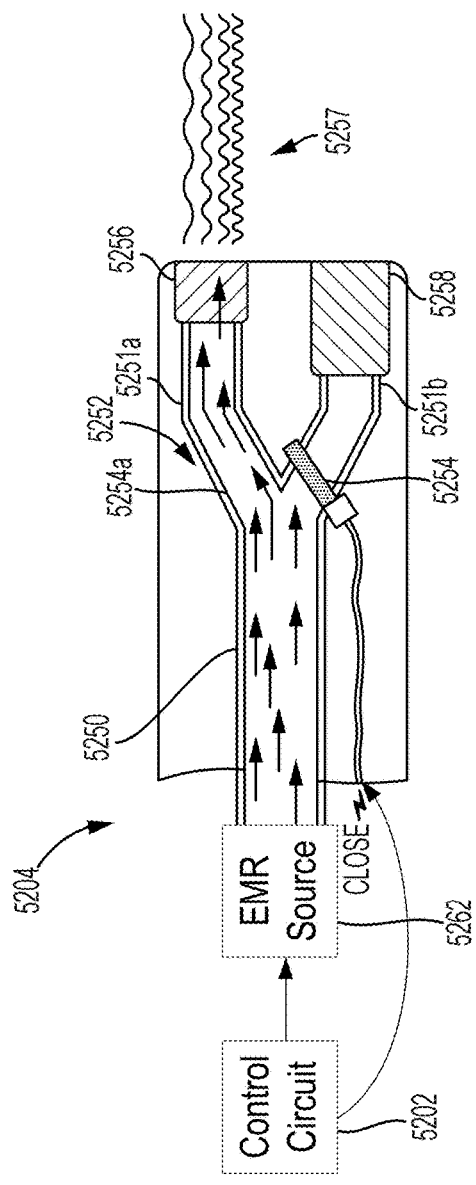

FIG. 31A illustrates a diagram of an emitter assembly including a single EMR source, wherein the emitter assembly is in a first state, in accordance with at least one aspect of the present disclosure.

Figure 31B:
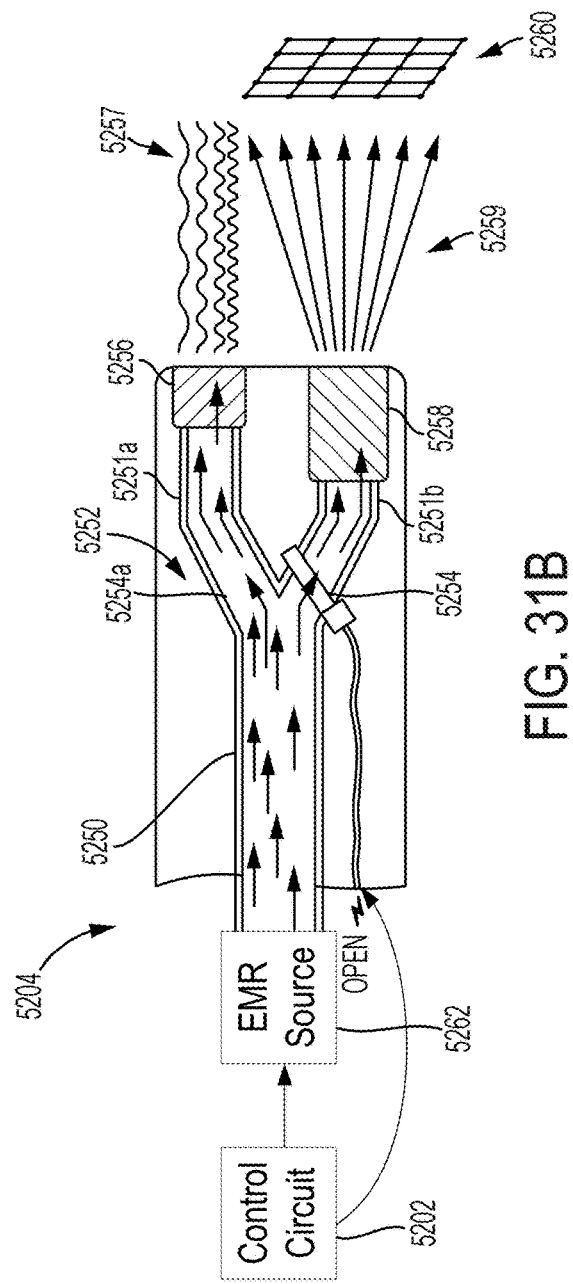

FIG. 31B illustrates a diagram of the emitter assembly of FIG. 31A, wherein the emitter assembly is in a second state, in accordance with at least one aspect of the present disclosure.

Figure 32:
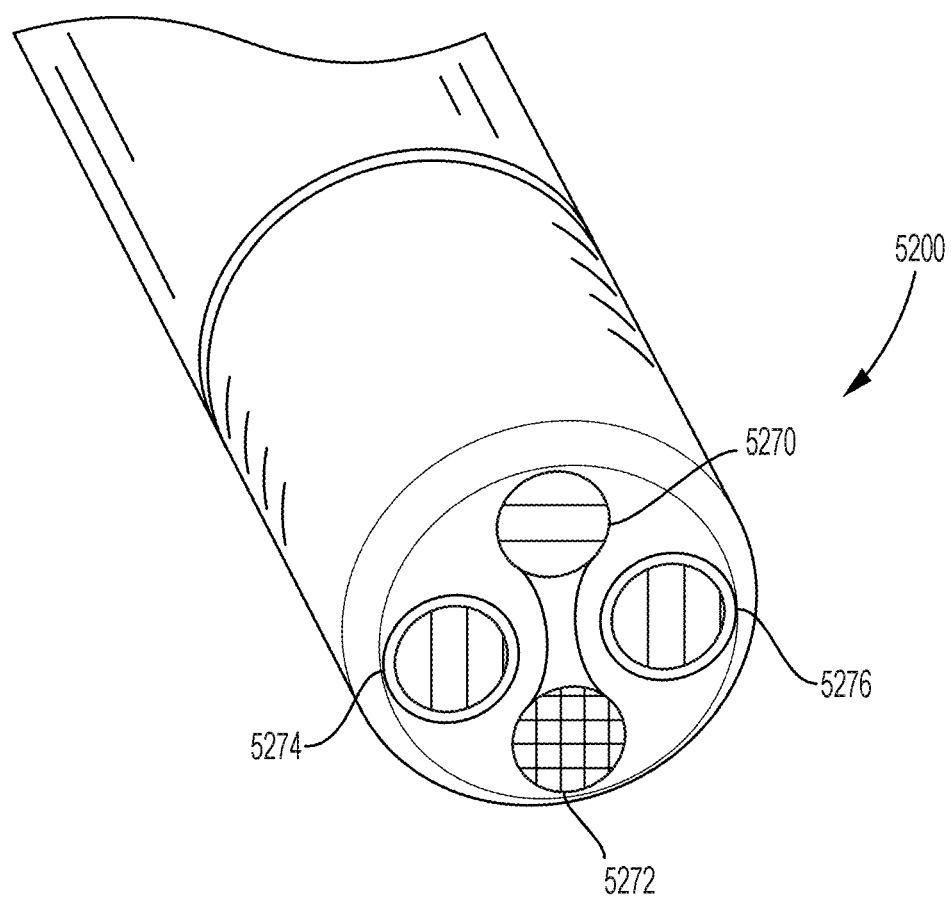

FIG. 32 illustrates a visualization system, including a combined multispectral and structured light source and 3D camera, in accordance with at least one aspect of the present disclosure.

DESCRIPTION

Applicant of the present application also owns the following U.S. Patent Applications, filed on Sep. 11, 2018, each of which is herein incorporated by reference in its entirety:

U.S. patent application Ser. No. 16/128,179, titled SURGICAL VISUALIZATION PLATFORM;
U.S. patent application Ser. No. 16/128,191, titled SURGICAL VISUALIZATION CONTROLS;
U.S. patent application Ser. No. 16/128,198, titled COMBINATION EMITTER AND CAMERA ASSEMBLY;
U.S. patent application Ser. No. 16/128,207, titled SINGULAR EMR SOURCE WITH DUAL OUTPUT EMITTER ASSEMBLY;

U.S. patent application Ser. No. 16/128,176, titled SURGICAL VISUALIZATION WITH PROXIMITY TRACKING FEATURES;

U.S. patent application Ser. No. 16/128,187, titled SURGICAL VISUALIZATION OF MULTIPLE TARGETS;

U.S. patent application Ser. No. 16/128,192, titled VISUALIZATION OF SURGICAL DEVICES;

U.S. patent application Ser. No. 16/128,163, titled OPERATIVE COMMUNICATION OF LIGHT;

U.S. patent application Ser. No. 16/128,197, titled ROBOTIC LIGHT PROJECTION TOOLS;

U.S. patent application Ser. No. 16/128,164, titled SURGICAL VISUALIZATION FEEDBACK SYSTEM;

U.S. patent application Ser. No. 16/128,193, titled SURGICAL VISUALIZATION AND MONITORING;

U.S. patent application Ser. No. 16/128,195, titled INTEGRATION OF IMAGING DATA;

U.S. patent application Ser. No. 16/128,170, titled ROBOTICALLY-ASSISTED SURGICAL SUTURING SYSTEMS;

U.S. patent application Ser. No. 16/128,183, titled SAFETY LOGIC FOR SURGICAL SUTURING SYSTEMS;

U.S. patent application Ser. No. 16/128,172, titled ROBOTIC SYSTEMS WITH SEPARATE PHOTOACOUSTIC RECEIVERS, Robotic system with separate photoacoustic receiver; and U.S. patent application Ser. No. 16/128,185, titled FORCE SENSOR THROUGH STRUCTURED LIGHT DEFLECTION.

Applicant of the present application also owns U.S. Pat. No. 9,072,535, titled SURGICAL STAPLING INSTRUMENTS WITH ROTATABLE STAPLE DEPLOYMENT ARRANGEMENTS, issued Jul. 7, 2015, which is incorporated by reference herein in its entirety.

Applicant of the present application also owns U.S. Provisional Patent Application No. 62/611,339, titled ROBOT ASSISTED SURGICAL PLATFORM, filed Dec. 28, 2017, which is incorporated by reference herein in its entirety.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,711, titled SENSING ARRANGEMENTS FOR ROBOT-ASSISTED SURGICAL PLATFORMS; and U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following—described aspects, expressions of aspects, and/or examples, can be combined with any one or more of the other following-described aspects, expressions of aspects, and/or examples.

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein. Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

These and other related topics are described herein and/or in the aforementioned contemporaneously-filed U.S. Patent Applications, which are incorporated by reference herein in their respective entireties.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
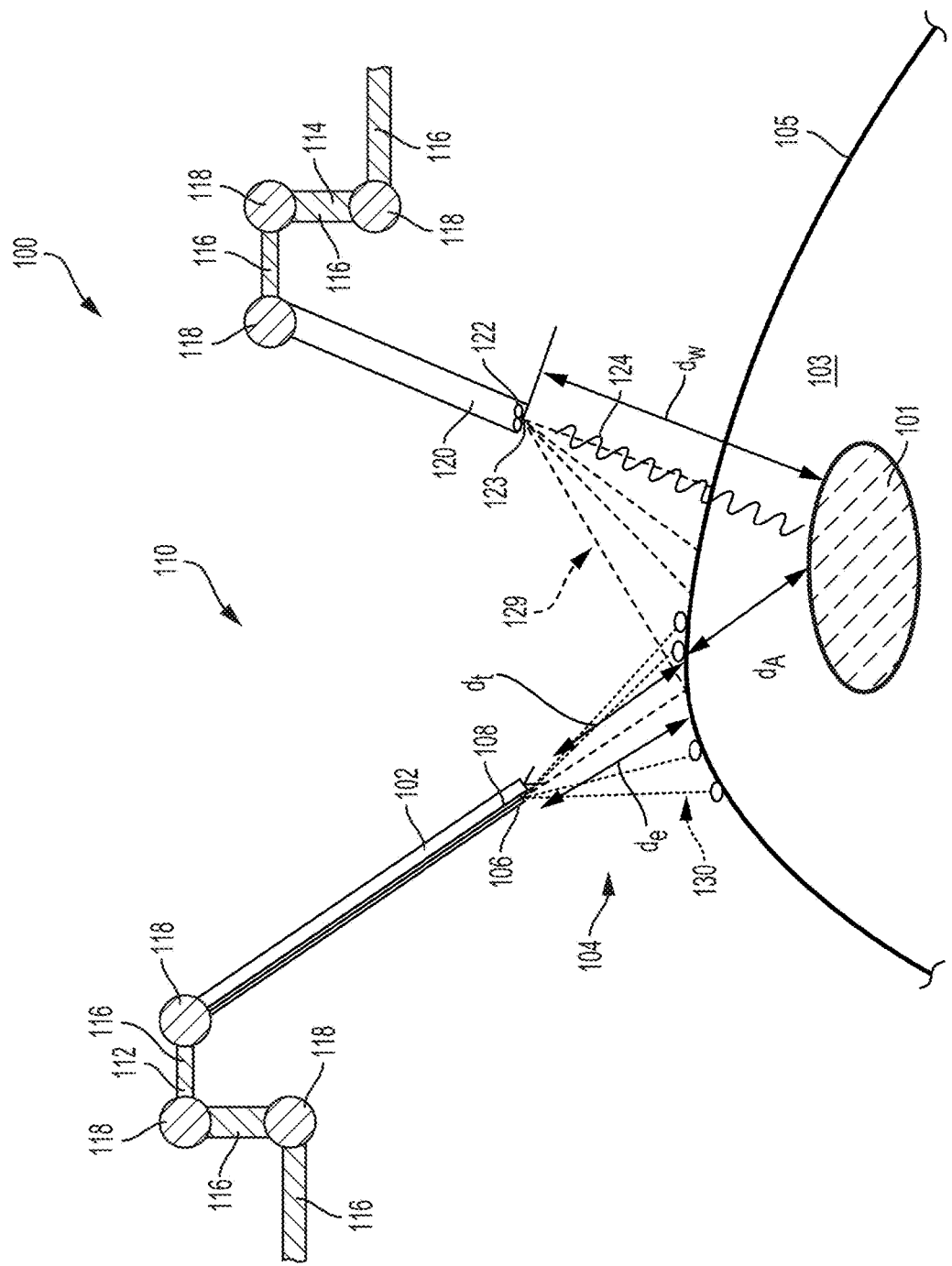
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intraoperatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
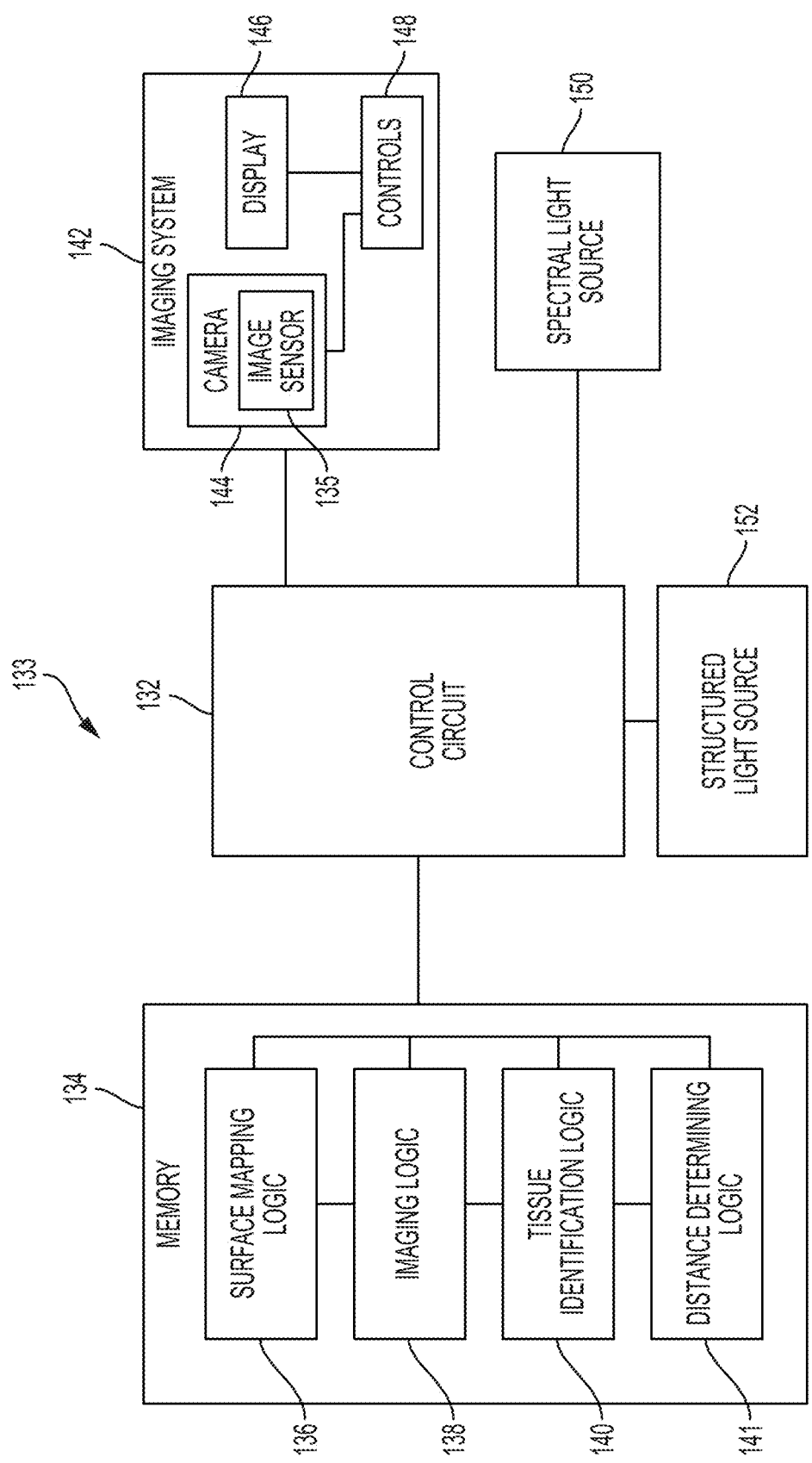
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
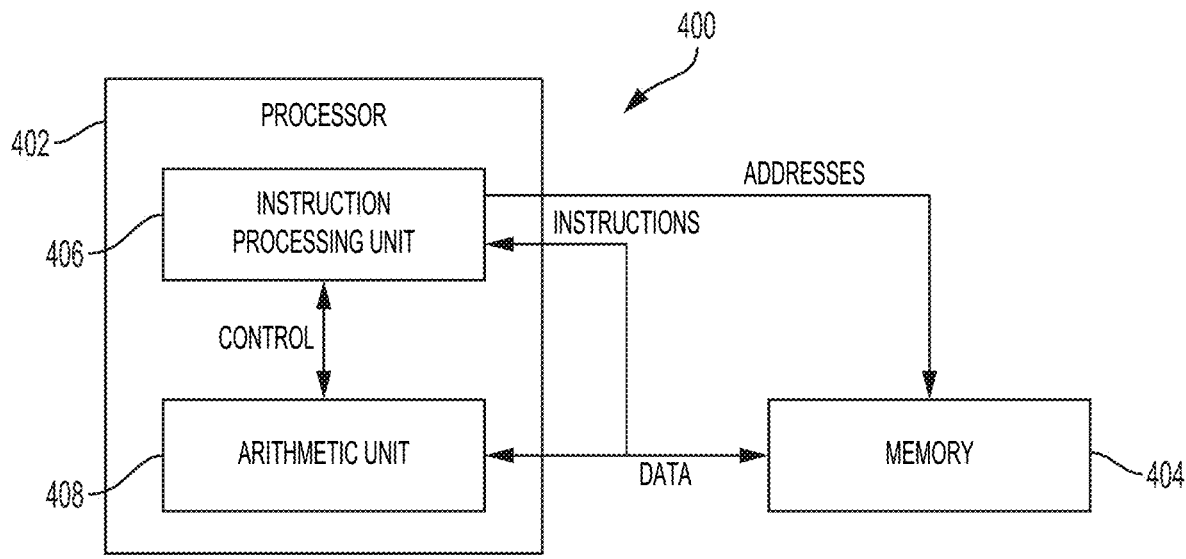
FIG. 2A illustrates a control circuit configured to control aspects of a surgical visualization system, according to at least one aspect of the present disclosure.
Figure 2B:
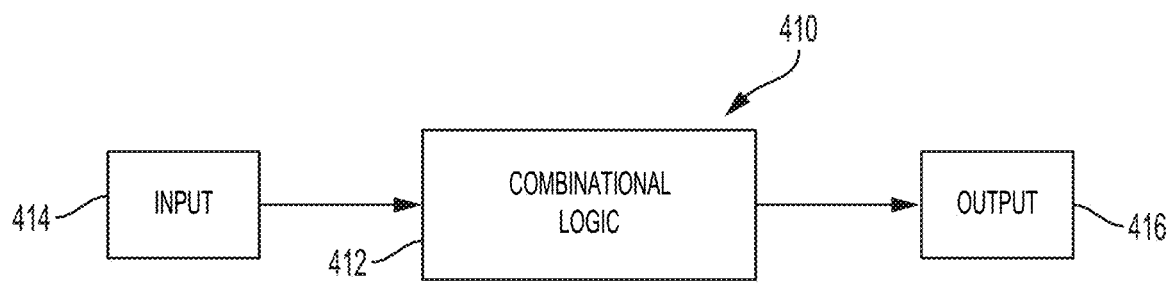
FIG. 2B illustrates a combinational logic circuit configured to control aspects of a surgical visualization system, according to at least one aspect of the present disclosure.
Figure 2C:
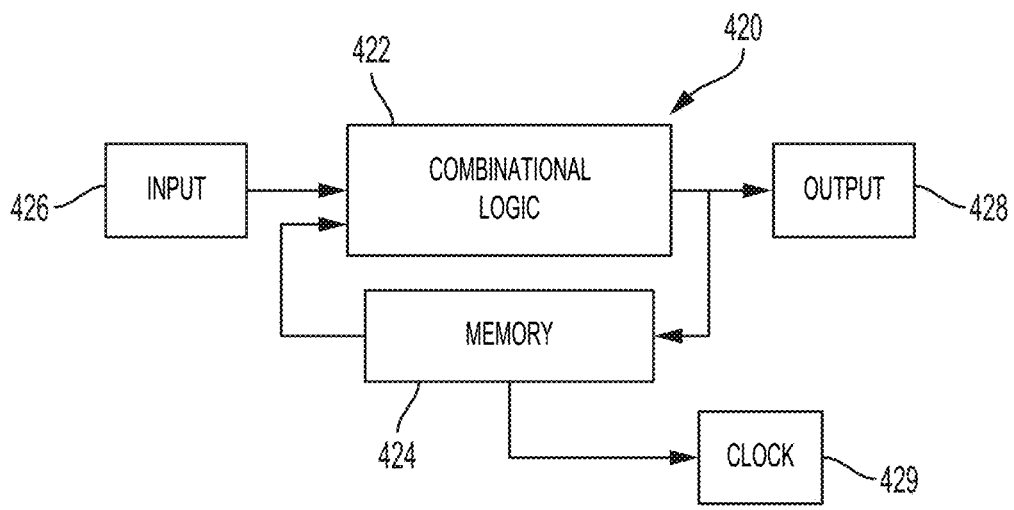
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned contemporaneously-filed U.S. Patent Applications, including U.S. patent application Ser. No. 16/128,192, titled VISUALIZATION OF SURGICAL DEVICES, for example, which are incorporated by reference herein in their respective entireties.

In one aspect, the critical structure 101 may be embedded in tissue 103. Stated differently, the critical structure 101 may be positioned below the surface 105 of the tissue 103. In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closed-loop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
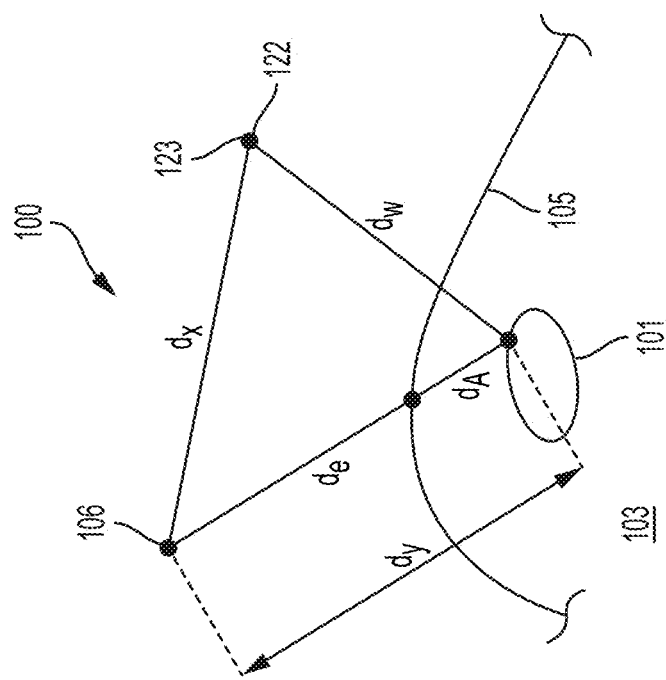
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$.

Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
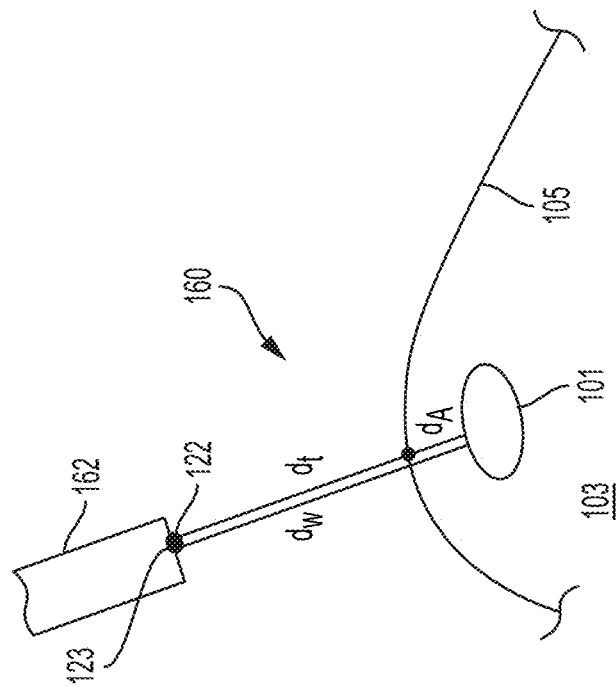
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figures 7A, 7B:
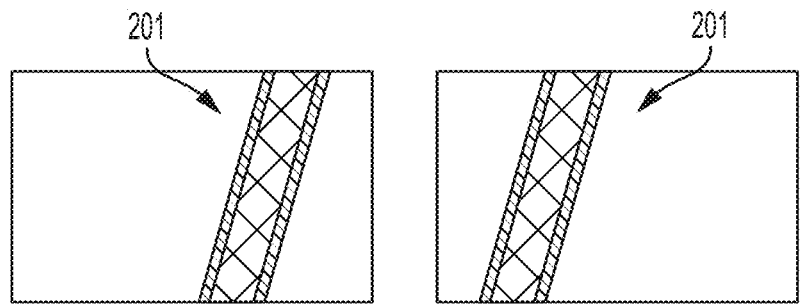
Figure 8:
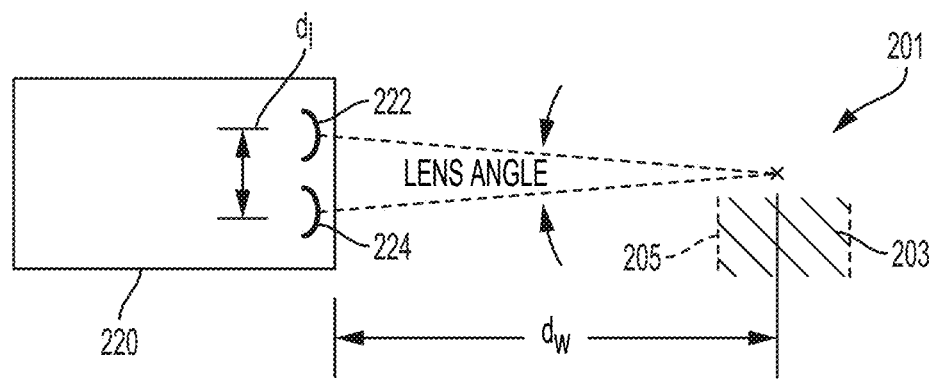
FIG. 8 is a schematic of the surgical visualization system of FIG. 6, in which a camera-to-critical structure distance $d_w$ from the three-dimensional camera to the critical structure can be determined, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIG. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
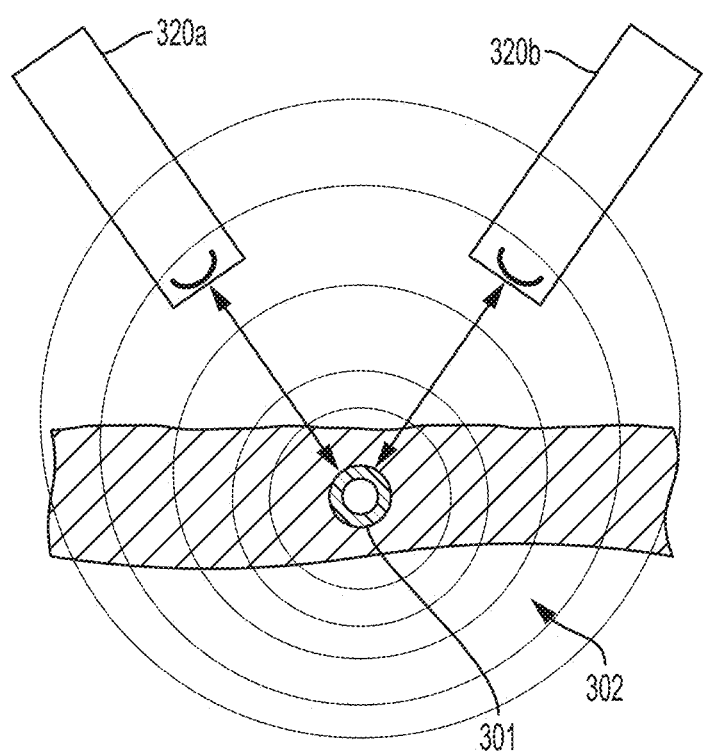
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
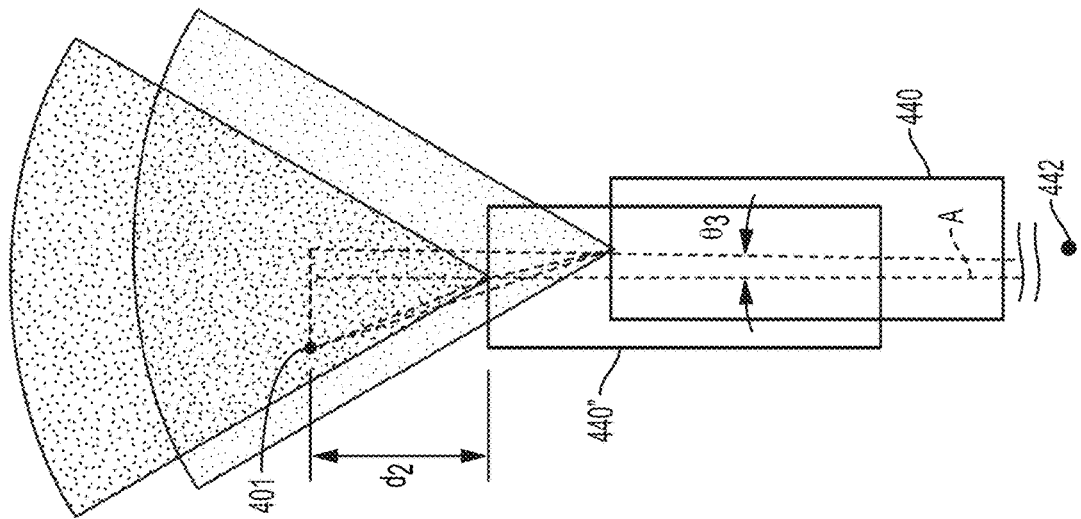
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
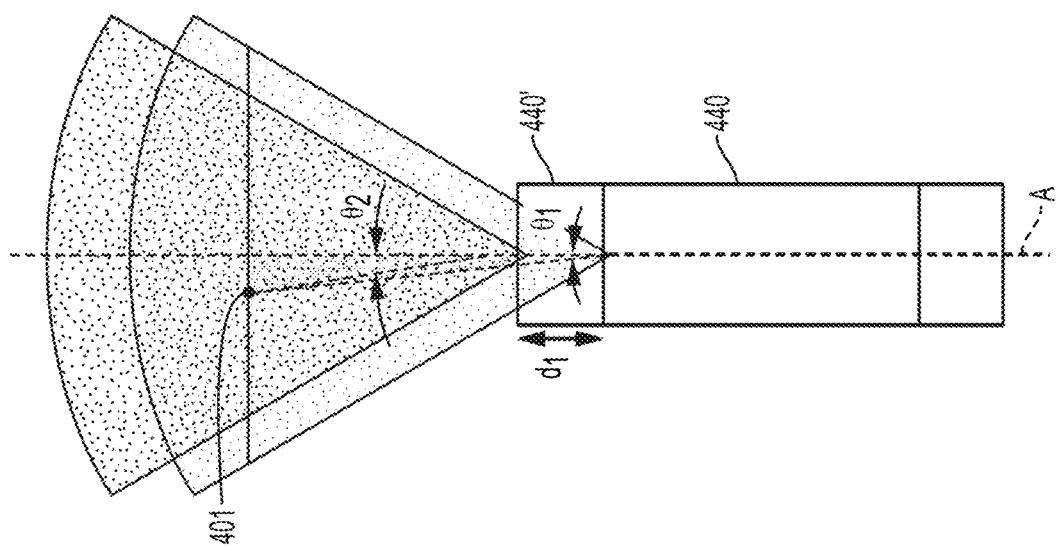
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta_3$ about the axis A. A pivot point 442 for rotation of the camera 440 is positioned at the cannula/patient interface. In FIG. 10B, the camera 440 is translated and rotated to a location 440". As the camera 440 moves and the edge of view changes with respect to the critical structure 401, the distance to the critical structure 401 can be calculated. In FIG. 10B, a distance $d_2$ can be 9.01 mm, for example, and the angle $\theta_3$ can be 0.9 degrees, for example.

Figure 5:
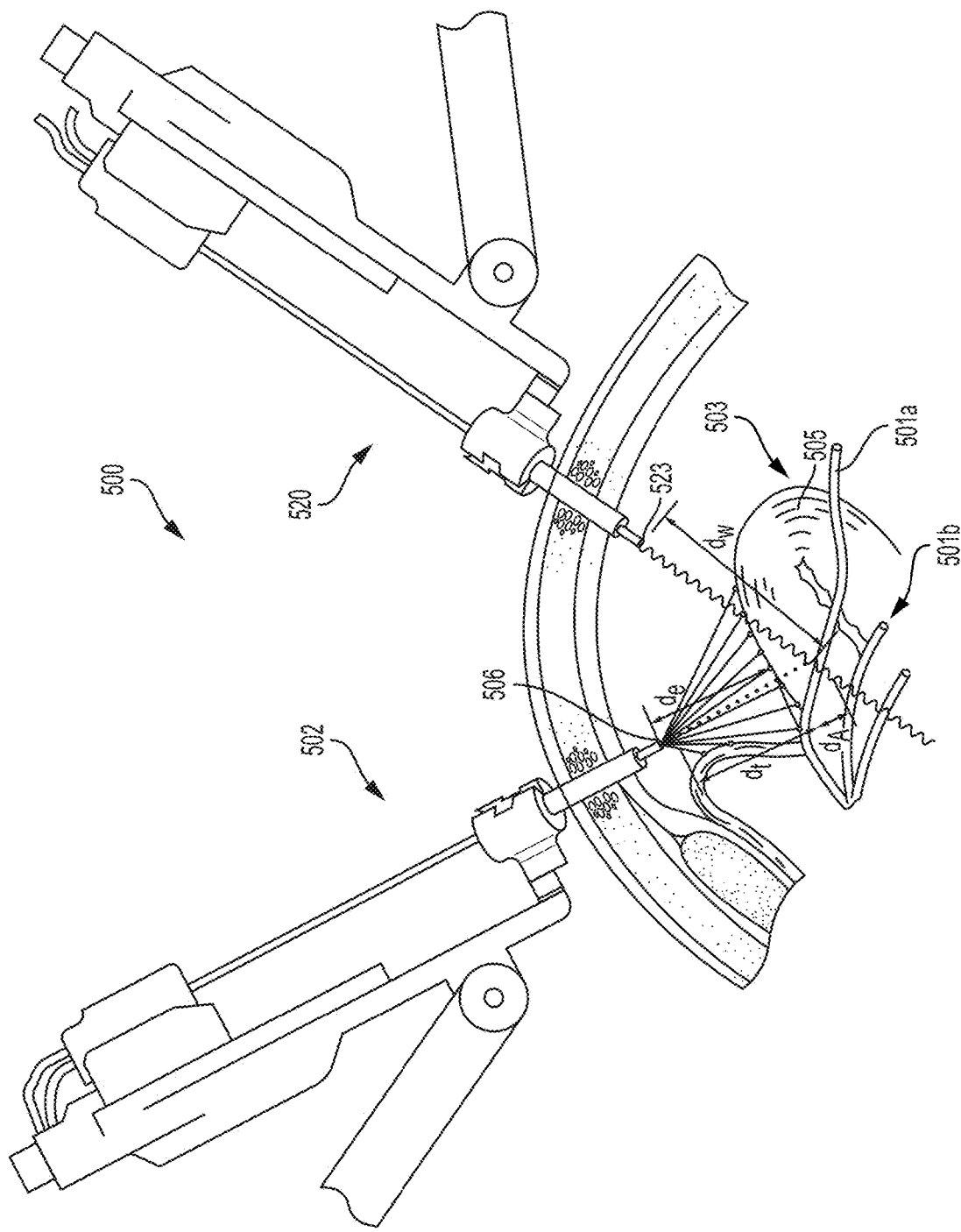
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera—to ureter distance $d_w$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
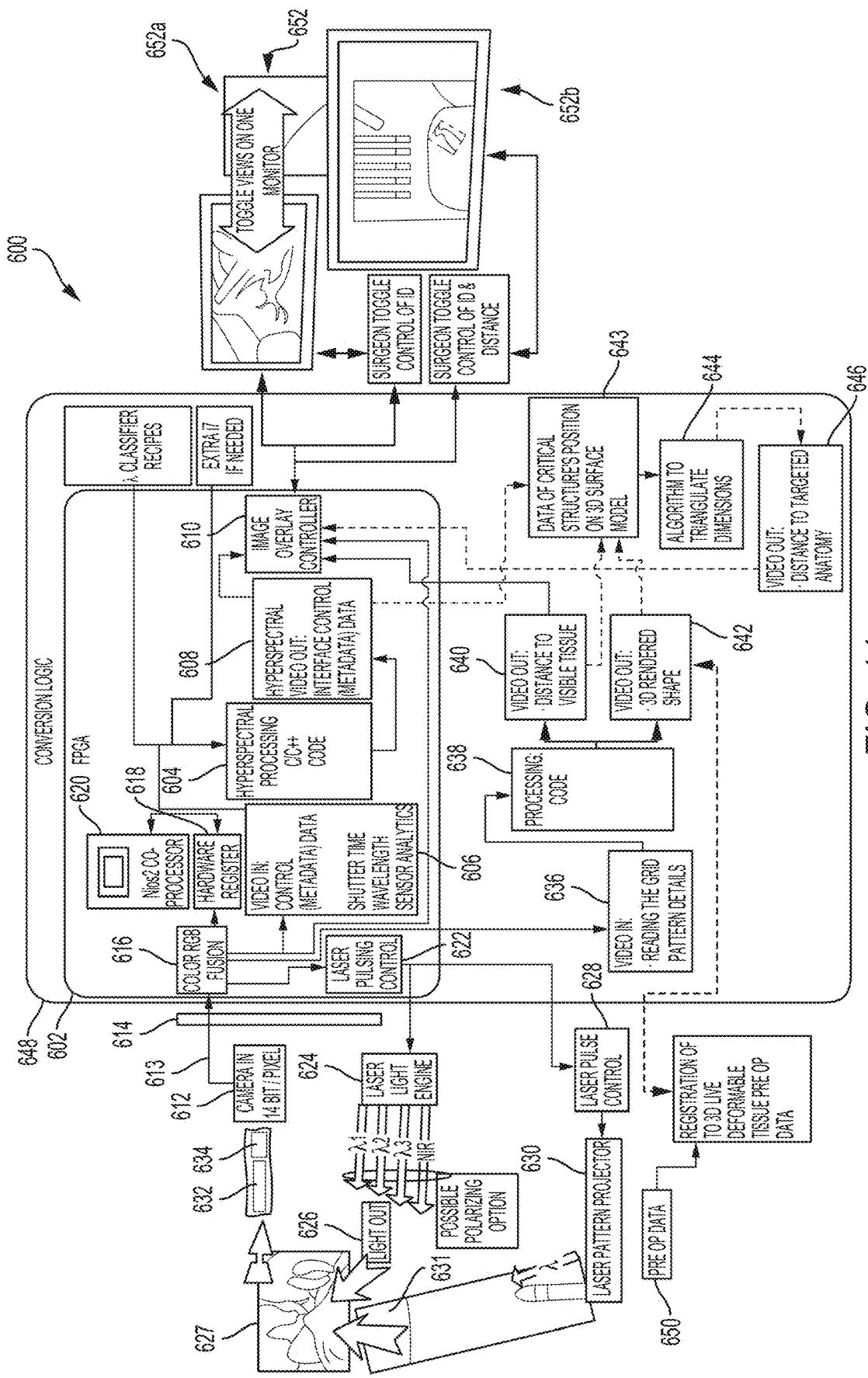
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned contemporaneously-filed U.S. Patent Applications, including U.S. patent application Ser. No. 16/128,195, titled INTEGRATION OF IMAGING DATA, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
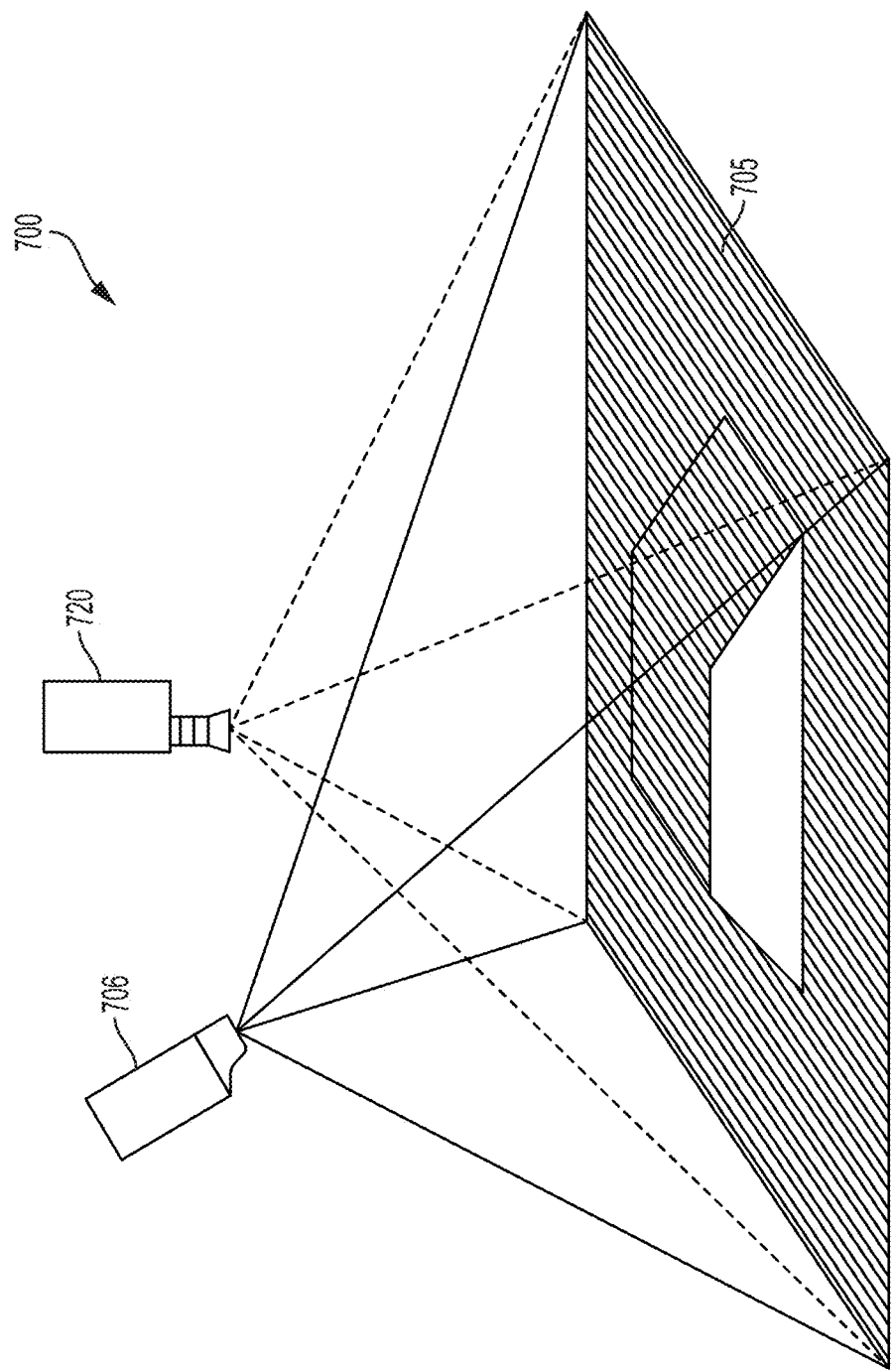
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured_light.

Figure 13:
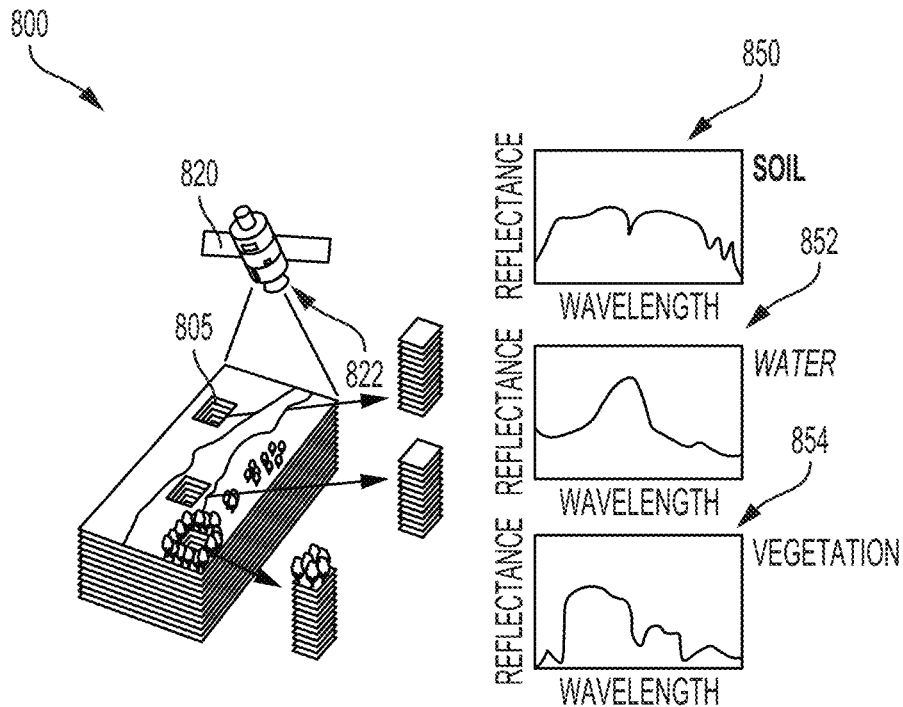
FIG. 13 is a schematic of a hyperspectral visualization system for imaging terrestrial features or objects, according to at least one aspect of the present disclosure.

Referring now to FIG. 13, by way example to illustrate the concept of hyperspectral imaging, a terrestrial hyperspectral imaging system 800 is shown. The terrestrial hyperspectral imaging system 800 is configured to image terrestrial features or objects, such as soil, water, and/or vegetation, for example. The terrestrial hyperspectral imaging system 700 includes a space-borne hyperspectral sensor 822 on a spacecraft 820 to conduct hyperspectral imaging of a portion of the Earth's surface 805. The spectral dimension includes several layers. Each pixel of the images contains a sampled spectrum that is used to identify the materials present in the pixel by their reflectance. The data can be converted to graphical representations 850, 852, 854 of reflectance as a function of wavelength for soil, water, and vegetation, respectively, for example. Terrestrial hyperspectral imaging is further described at www.markelowitz.com/Hyperspectral.html.

Figure 14:
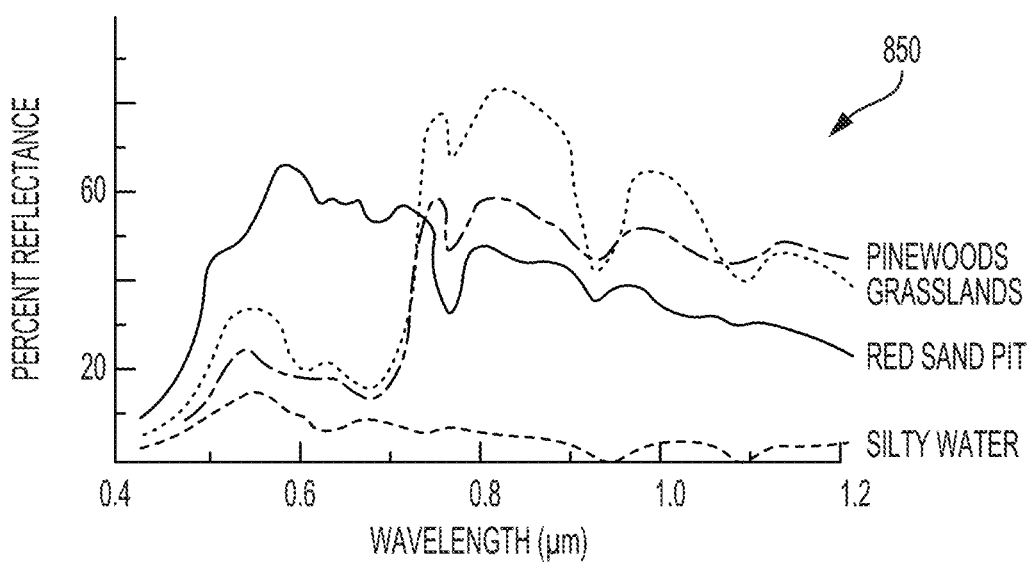
FIG. 14 is a graphical representation of hyperspectral signatures for various terrestrial features or objects, according to at least one aspect of the present disclosure.

Also by way example to illustrate the concept of hyperspectral imaging, FIG. 14 is a graphical representation 850 of hyperspectral signatures for various terrestrial features or objects, according to at least one aspect of the present disclosure. Percent reflectance is shown along the vertical axis and wavelength (nm) is shown along the horizontal axis. As shown, each object—pinewoods, grasslands, red sand pit, and silty water—has a unique hyperspectral signature that can be used to identify the object.

The hyperspectral imaging concepts described in connection with FIGS. 13 and 14 may be employed for different materials that have different wavelengths and bands of absorption, according to at least one aspect of the present disclosure. The following table illustrates the wavelengths and bands of absorption for various materials. A first range of wavelengths between 400 nm and 700 nm represents the visible light spectrum. A second range of wavelengths between 700 nm and 1400 nm represents the near infrared (NIR) spectrum. A third range of wavelengths between 1400 nm and 3000 nm represents a shortwave infrared (SWIR) spectrum. A first band centered at 1250 nm represents iron absorption and leaf moisture content. A second band between 1500 nm and 1750 nm represents plastics, fiberglass, and petroleum. A third band between 200 nm and 2400 nm represents mineral ID.

TABLE 1 specifies wavelengths and bands of absorption for various materials.

TABLE 1

| Wavelength (nm) | Region | Band(s) | Material |
| --- | --- | --- | --- |
| 400-700 | Visible | | |
| 700-1400 | NIR | | |
| 1400-3000 | SWIR | 1 - centered at 1250 | Iron adsorption |
| | | | Leaf moisture content |
| | | 2 - 1500-1750 | Plastics |
| | | | Fiberglass |
| | | | Petroleum |
| | | 3 - 200-2400 nm | Mineral ID |

Referring now to FIGS. 15A-15C, as a further illustration of hyperspectral imaging concepts, tests were conducted in which spectral imaging was applied to a fried egg 952. An image of the fried egg 952 with a yellow egg yolk 954 and an egg white 956 surrounding the egg yolk 954 is shown in FIG. 15A. A graphical representation 950 of spectral signatures for the fried egg 952 are shown in FIG. 15B. Specifically, the graphical representation 950 shows absorption units versus wavelength (nm) for the egg yolk 954 and the egg white 956 of the fried egg 952. In FIG. 15C, a spectral image (in black-and-white) of the fried egg 952 is shown, in which the image is augmented to differentiate between the egg yolk portion and the egg white portion based on the hyperspectral signature data.

In various instances, hyperspectral imaging technology, as described herein for illustrative purposes with respect to terrestrial features and objects and a fried egg, can be employed to identify signatures in anatomical structures in order to differentiate a critical structure from obscurants. Hyperspectral imaging technology may provide a visualization system that can provide a way to identify critical structures such as ureters and/or blood vessels, for example, especially when those structures are obscured by fat, connective tissue, blood, or other organs, for example. The use of the difference in reflectance of different wavelengths in the infrared (IR) spectrum may be employed to determine the presence of key structures versus obscurants. Referring now to FIGS. 16-18, illustrative hyperspectral signatures for a ureter, an artery, and nerve tissue with respect to obscurants such as fat, lung tissue, and blood, for example, are depicted.

FIG. 16 is a graphical representation 1050 of an illustrative ureter signature versus obscurants. The plots represent reflectance as a function of wavelength (nm) for wavelengths for fat, lung tissue, blood, and a ureter. FIG. 17 is a graphical representation 1052 of an illustrative artery signature versus obscurants. The plots represent reflectance as a function of wavelength (nm) for fat, lung tissue, blood, and a vessel. FIG. 18 is a graphical representation 1054 of an illustrative nerve signature versus obscurants. The plots represent reflectance as a function of wavelength (nm) for fat, lung tissue, blood, and a nerve.

In various instances, select wavelengths for spectral imaging can be identified and utilized based on the anticipated critical structures and/or obscurants at a surgical site (i.e. "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 19 and 20, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 20, for example, which can be measured by the receiver 1108.

Based on the delay between the emitted wave 1124 and the received wave 1125, the time-of-flight sensor system 1104 is configured to determine the distance d (FIG. 19). A time-of-flight timing diagram 1130 for the emitter 1106 and the receiver 1108 of FIG. 19 is shown in FIG. 20. The delay is a function of the distance d and the distance d is given by:

$$d = \frac{ct}{2} \cdot \frac{q_2}{q_1 + q_2}$$

where:
  c=the speed of light;
  t=length of pulse;
  $q_1$=accumulated charge while light is emitted; and
  $q_2$=accumulated charge while light is not being emitted.

As provided herein, the time-of-flight of the waveforms 1124, 1125 corresponds to the distance d in FIG. 19. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t$$

where:
  $d_A$=the depth of the critical structure 1101;
  $d_w$=the distance from the emitter 1106 to the critical structure 1101 (d in FIG. 19); and $d_{t1}$=the distance from the emitter 1106 (on the distal end of the surgical device 1102) to the surface 1105 of the obscuring tissue 1103.

In one aspect of the present disclosure, referring now to FIG. 21, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described herein and in the aforementioned contemporaneously-filed U.S. Patent Applications, which are incorporated by reference herein in their respective entireties.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}$, $d_{2a}$, $d_{3a}$, $d_{1b}$, $d_{2b}$, $d_{2c}$ indicated in FIG. 21.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}$, $d_{2a}$, $d_{3a}$, $d_{1b}$, $d_{2b}$, $d_{2c}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}$, $d_{2a}$, $d_{3a}$, $d_{1b}$, $d_{2b}$, $d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 21, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 21, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013 vol. 138 no. 3 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization system disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure(s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

Controlling an Emitter Assembly Pulse Sequence

FIG. 22 illustrates a block diagram of a visualization system 5200 for intraoperative identification of structures, in accordance with at least one aspect of the present disclosure. The visualization system 5200 is configured to visualize structures that may be obscured by fluid (e.g., blood), tissue (e.g., adipose tissue, connective tissue, or collections of tissue, such as organs), and/or other structures in order to identify critical structures during the course of a surgical procedure, such as ureters, blood vessels, pulsing structured light, infrared radiation (IR), and visible light in various sequences and combinations. In the following description of the visualization system 5200, reference should also be made to FIGS. 1, 2, and 11.

In one aspect, the visualization system 5200 includes a receiver assembly 5206, which can include the receiver 108 (FIG. 1) and/or the camera 612 including an image sensor 634 (FIG. 11), and an emitter assembly 5204, which can include the optical waveform emitter 123 (FIG. 1) and/or the laser light engine 624 (FIG. 11). Further, the visualization system 5200 can include a control circuit 5202, which can include the control circuit 132 (FIG. 2) and/or the spectral control circuit 602 (FIG. 11), coupled to each of the emitter assembly 5204 and the receiver assembly 5206. As described above, the emitter assembly 5204 can be configured to emit EMR at a variety of wavelengths (e.g., in the visible spectrum and/or in the IR spectrum) and/or as structured light (i.e., EMR projected in a particular known pattern). The control circuit 5202 can include, for example, hardwired circuitry, programmable circuitry (e.g., a computer processor coupled to a memory or field programmable gate array), state machine circuitry, firmware storing instructions executed by programmable circuitry, and any combination thereof.

In one aspect, the emitter assembly 5204 can be positioned on or adjacently to an end effector 5208 of a surgical instrument 5209, as depicted in FIG. 23, for example. The emitter assembly 5204 can include, for example, a first emitter 5212 for emitting visible light and a second emitter 5214 for emitting structured light. The emitters 5212, 5214 can include various filters for emitting EMR at desired wavelengths. In another aspect, the receiver assembly 5206 can be positioned on or adjacently to an end effector 5208 of a surgical instrument 5209. In another aspect, the emitter assembly 5204 can be a distinct surgical instrument, as depicted in FIGS. 1-12, for example. In another aspect, the emitter assembly 5204 and/or receiver assembly 5206 can be positioned on one or more robotic arms that are components of or separate from a main robotic system. In various aspects, the robotic arms can be configured to be manually positionable (with or without assistance from the robotic system servomotor) and further configured to register their relative position (e.g., as Cartesian coordinates) as they are positioned so that the visualization system 5200 can track the relative positions of the receiver assembly 5206 and emitter assembly 5204 for calculating positions of visualized structures, as described in connection with FIGS. 1-12.

In various aspects, the surgical visualization system 5200 is configured to detect and avoid critical structures during surgical approach and dissection. Generally, the surgical visualization system 5200 includes a specialized receiver assembly 5206 (e.g., camera 612 including optics 632 and an image sensor 634) with feedback control of an emitter assembly 5204 (e.g., laser light engine 624). The receiver assembly 5206 can include, for example, a 3D camera sensor array configured to sense a combination of structured light, visible light, ultraviolet, and/or IR. By controlling the emitter assembly 5204 to sequentially pulse structured light, visible light, and non-visible EMR, all three different types of EMR can be combined in a single visualization system 5200 to visualize and track tissues, structures, tools, and other objects during the course of a surgical procedure (e.g., a minimally invasive surgical procedure). It will be appreciated that multiple similarly configured cameras can be utilized to visualize and track multiple tissues, structures, tools, and other objects during the course of a surgical procedure.

The control circuit 5202 can be configured to control the emitter assembly 5204 to emit or pulse visible light 5205a, IR 5205b, and/or structured light 5205c in various sequences and combinations, as is described in further detail below. Further, the control circuit 5202 can be configured to determine information related to the tissue at which the emitter assembly 5204 is directing the emitted EMR by receiving the reflected visible light 5207a, reflected IR 5207b, and/or reflected structured light 5207c via the receiver assembly 5206. For example, structured light can be utilized to determine the distance and shape data of the surface(s) against which the structured light is projected, visible light can provide 3D image data, and nonvisible light (e.g., IR) can provide hyperspectral data of hidden anatomy due to the differences in absorption bands of different tissues and other structures. As described above in FIGS. 16-18, for example, the data determined from the emitted structured, visible, and/or nonvisible EMR can be utilized to distinguish between physiological types of tissue and determine other tissue information. Further, the control circuit 5202 can be configured to implement a feedback loop or algorithm to control the sequence and/or composition of the EMR that is pulsed by the emitter assembly 5204 according to tissue information (e.g., tissue type or other tissue parameters) determined from the reflected structured, visible, and/or nonvisible EMR, such as the process 5240 described in further detail below in connection with FIG. 28.

In various aspects, the emitter assembly 5204 can be configured to emit EMR at a plurality of wavelengths $\lambda_1, \lambda_2, \lambda_3, \ldots \lambda_n$ or range of wavelengths. In one illustrative application, the emitter assembly 5204 can be configured to emit EMR at a first wavelength $\lambda_1$ characterized as red light (i.e., long-wavelength visible light), a second wavelength $\lambda_2$ characterized as blue light (i.e., short-wavelength visible light), a third wavelength $\lambda_3$ characterized as green light (i.e., medium-wavelength visible light), a fourth wavelength $\lambda_4$ characterized as green light (can be different than the third wavelength $\lambda_3$), a fifth wavelength $\lambda_5$ utilized for structured light (e.g., green structured light), a sixth wavelength $\lambda_6$ characterized as near-IR radiation (NIR), a seventh wavelength $\lambda_7$ characterized as NIR (can be different than the sixth wavelength $\lambda_6$), and/or an eighth wavelength $\lambda_8$ characterized as short-wavelength IR (SWIR). The control circuit 5202 can be configured to control the emitter assembly 5204 to pulse EMR at various wavelengths $\lambda_1, \lambda_2, \lambda_3, \ldots \lambda_n$ in various sequences. As one example, the control circuit 5202 can be configured to control the emitter assembly 5204 to emit EMR at the third wavelength $\lambda_3$, then the first wavelength $\lambda_1$, then the second wavelength $\lambda_2$, then the fifth wavelength $\lambda_5$, then the seventh wavelength $\lambda_7$, and then the sixth wavelength $\lambda_6$. This sequence can represent, for example, a base or default sequence. In various aspects, the control circuit 5202 can be configured to control the emitter assembly 5204 to repeat the pulse sequence or modify the pulse sequence according to, for example, user input, data extracted from reflected EMR, and/or a control algorithm executed by the control circuit 5202. Further, the particular wavelengths of EMR emitted by the emitter assembly 5204 and/or the particular sequence wavelengths of EMR in the pulse sequence can be selected for specific purposes, such as visualizing particular types of structures. Accordingly, the particular pulse sequence emitted by the emitter assembly 5204 can be utilized to identify critical structures and/or determine the topography of the surgical site within the field of view (FOV) of the emitter assembly 5204.

In one aspect, the visualization system 5200 can be configured to visualize a user-selectable structure or tissue type. For example, FIG. 24 illustrates a logic flow diagram of a process 5220 for visualizing tissue structures, in accordance with at least one aspect of the present disclosure. In the following description of the process 5220, reference should also be made to FIGS. 22 and 25-27.

Accordingly, the control circuit 5202 receives 5222 a selected target tissue that is to be visualized by the visualization system 5200. The target tissue can be, for example, selected by a user of the visualization system 5200. In various examples, the control circuit 5202 may infer the target tissue from information regarding the surgical procedure being performed, such as via a situational awareness system as described in U.S. Provisional Patent Application No. 62/659,900, titled METHOD OF HUB COMMUNICATION, filed Apr. 19, 2018, which is hereby incorporated by reference herein in its entirety. Alternatively, or additionally, a user can select a tissue to be visualized via a control device coupled to the control circuit 5202, such as a control dial 5230 as depicted for illustrative purposes in FIGS. 25-27. Accordingly, the control circuit 5202 retrieves 5224 the pulse sequence of visible light, IR, and/or structured light corresponding to the selected target tissue from, for example, a memory 134 (FIG. 2) coupled to the control circuit 5202. The retrieved pulse sequence can dictate the particular wavelength(s) of EMR to be emitted by the emitter assembly 5204, the length of time that each wavelength is to be emitted, the sequence or arrangement in which the wavelengths are to be emitted, and so on.

Accordingly, the control circuit 5202 controls 5226 the emitter assembly 5204 to emit the particular combination of visible light, IR, and/or structured light in the particular sequence dictated by the retrieved 5224 pulse sequence. The control circuit 5202 can control 5226 the emitter assembly 5204 via, for example, a pulse controller, such as the laser pulsing control circuit 622 controlling a laser light engine 624, as is described above in connection with FIG. 11. When the emitter assembly 5204 is directed towards a surgical site, the control circuit 5202 can accordingly detect 5228 a response from the pulsed EMR signal(s) via the receiver assembly 5206, as discussed above in FIGS. 13-21, to visualize particular tissues and/or structures at the surgical site corresponding to the selected pulse sequence. According to the response intensity detected via the receiver assembly 5206, the control circuit 5202 can, for example, cause a display device 5232 to display or visualize the location and/or appearance of the tissue corresponding to the selected target tissue type. For example, FIG. 25 shows an illustrative application where the visualization system 5200 is being utilized to generally visualize a liver 5234 and where a user has selected (via a control device, such as a control dial 5230, coupled to the control circuit 5202 and/or emitter assembly 5204) tumor tissue to be highlighted or tagged.

Accordingly, the control circuit 5202 controls 5226 the emitter assembly 5204 to emit the pulse sequence appropriate for tumor tissue visualization so that any tumor tissue 5235 present within the FOV of the emitter assembly 5204 is highlighted or otherwise visualized on the display device 5232. In various aspects, tissue that does not correspond to the selected tissue type can either not be displayed on the display device 5232 or be non-emphasized, such as by being displayed in phantom, for example. As other examples, FIGS. 26 and 27 show illustrative applications of the visualization system 5200 where a user has selected (via, e.g., the control dial 5230) for duct tissue 5236 and vein tissue 5237, respectively, to be visualized in the manner described above.

In various aspects, the control circuit 5202 is configured to track or tag a target tissue by repeating the pulse sequence associated with the target tissue and spatially tracking the movement of the tissue structure on the associated display device 5232. For example, a distinguishing color can be assigned to target tissue that is being tracked or the target tissue that is being tracked can be rendered normally and all other tissue structures can be displayed in phantom, as depicted in FIGS. 25-27. In various aspects, the control circuit 5202 is configured to track or tag surgical instruments and other non-tissue objects within the FOV of the emitter assembly 5204 by repeating the pulse sequence associated with the object and spatially tracking the movement of the object on the associated display device 5232. The control circuit 5202 can detect the presence according to the particular EMR response intensities at particular wavelengths corresponding to the particular object, as described herein.

In another aspect, the visualization system 5200 can be configured to automatically visualize particular structures or tissue types by sweeping a range of pulsed wavelengths and then modifying the emitted EMR pulse sequence via a feedback loop according to the response intensities detected via the receiver assembly 5206. For example, FIG. 28 illustrates a logic flow diagram of a process 5240 for automatically visualizing structures, in accordance with at least one aspect of the present disclosure.

Accordingly, the control circuit 5202 controls 5242 the emitter assembly 5204 to emit a particular combination of visible light, IR, and/or structured light in a particular sequence. The control circuit 5202 can control 5226 the emitter assembly 5204 via, for example, a pulse controller, such as the laser pulsing control circuit 622 controlling a laser light engine 624, as is described above in connection with FIG. 11. The initial sequence and/or combination of pulsed EMR can be defined by a base or default pulse sequence that can be, for example, retrieved from a memory 134 (FIG. 2) by the control circuit 5202 upon activation of the visualization system 5200 or initiation by a user. When utilized during a surgical procedure, the emitter assembly 5204 can be directed towards a surgical site. Accordingly, the control circuit 5202 can detect 5244 a response from the pulsed EMR signal(s) via the receiver assembly 5206, as discussed above in FIGS. 13-21. According to the detected 5244 EMR response intensities, the control circuit 5202 can execute a detection algorithm to identify what is being detected at the surgical site and then modify 5246 the EMR pulse sequence emitted by the emitter assembly 5204 accordingly, such as via a pulse controller. As described above in connection with FIGS. 16-18, for example, a detection algorithm can distinguish between and identify various structures at a surgical site according to the detected response intensities at particular wavelengths. For example, a detection algorithm can be configured to identify vessels, ureters, and/or nerves given obscurants (e.g., fat and/or connective tissue) according to the detected response intensities. According to the tissue information determined from the EMR response intensities at particular wavelengths, the control circuit 5202 can then modify 5246 the EMR pulse sequence emitted by the emitter assembly 5204 to correspond to the particular detected tissue structures/information. For example, if the control circuit 5202 controls the emitter assembly 5204 to sweep a range of EMR wavelengths and consequently determines that the detected 5244 response indicates that tumor tissue is present, the control circuit 5202 can then modify 5246 the EMR pulse sequence to correspond to tumor tissue so that the detected tumor tissue is visualized on the user display.

In one aspect, the control circuit 5202 can be configured to control 5242 the emitter assembly 5204 to sweep a range of wavelengths in the EMR spectrum (in either structured or non-structured forms) and then determine at which wavelengths it detects 5244 the strongest response(s). The control circuit 5202 can then, for example, determine the tissue types and other tissue information that correspond to the detected response(s) and modify 5246 the EMR pulse sequence emitted by the emitter assembly 5204 to correspond to the tissue type, as described above.

Singular EMR Source Emitter Assembly

In one aspect, the emitter assembly 5204 can be configured to emit visible light, IR, and/or structured light from a single EMR source 5262. For example, FIGS. 29A and 29B illustrate a diagram of an emitter assembly 5204 in alternative states, in accordance with at least one aspect of the present disclosure. In this aspect, the emitter assembly 5204 comprises a channel 5250 connecting an EMR source 5262 to a first emitter 5256 configured to emit visible light (e.g., RGB) and/or IR 5257 and a second emitter 5258 configured to emit structured light 5259 in response to being supplied EMR of particular wavelengths from the EMR source 5262. The channel 5250 can include, for example, a fiber optic cable. The EMR source 5262 can include, for example, a laser light engine 624 (FIG. 11). The second emitter 5258 can include a filter configured to emit EMR from the EMR source 5262 as structured light 5259 to cause the emitter assembly 5204 to project a predetermined pattern 5260 onto the target site.

The emitter assembly 5204 further includes a light valve assembly 5252 configured to control whether EMR emitted from the EMR source 5262 proceeds to the first emitter 5256 and/or the second emitter 5258. In the depicted aspect, the light valve assembly 5252 is positioned at a bifurcation of the channel 5250 and includes a first light valve 5254a configured to control whether EMR from the EMR source 5262 is transmitted through a first branch 5251a to the first emitter 5256 and a second light valve 5254b configured to control whether EMR from the EMR source 5262 is transmitted to a second branch 5251b the second emitter 5258. The light valves 5254a, 5254b can include, for example, liquid crystal light valves having an EMR transmissivity that is controllable in response to an applied voltage or control signal. For example, liquid crystal light valves can be opaque when a first voltage or control signal is applied thereto and can be translucent when a second voltage or control signal is applied thereto.

In one aspect, the control circuit 5202 can be electrically coupled to the light valve assembly 5252 such that it can control the transmissivity of the light valves 5254a, 5254b via applying voltages or control signals thereto. The control circuit 5202 can be configured to control the light valve assembly 5252 to direct EMR from the EMR source 5262 to one or both of the emitters 5256, 5258 in response to, for example, user input and/or detected parameters (e.g., parameters associated with the surgical instrument or the surgical site). In one aspect, the control circuit 5202 is coupled to the EMR source 5262 such that it can control the wavelength of the EMR generated by the EMR source 5262. In various aspects, the control circuit 5202 can control the EMR source 5262 and the light valve assembly 5252 either independently or in tandem with each other.

In some aspects, the control circuit 5202 can adjust the wavelength of the EMR generated by the EMR source 5262 according to which light valve(s) 5254a, 5254b are opened (i.e., translucent) or closed (i.e., opaque). In other words, the control circuit 5202 can control the EMR source 5262 so that it produces EMR at a particular wavelength or within a particular wavelength range appropriate for whichever emitter 5254a, 5254b the EMR from the EMR source 5262 is directed by the light valve assembly 5252. For example, in FIG. 29A the control circuit 5202 has applied control signals to the light valve assembly 5252 to cause the first light valve 5254a to be translucent and the second light valve 5254b to be opaque. Further, the control circuit 5202 has controlled the EMR source 5262 to cause it to emit EMR at a first wavelength $\lambda_1$. Conversely, in FIG. 29B the control circuit 5202 has applied control signals to the light valve assembly 5252 to cause the second light valve 5254b to be translucent and the first light valve 5254a to be opaque. Further, the control circuit 5202 has controlled the EMR source 5262 to cause it to emit EMR at a second wavelength $\lambda_2$. In some aspects, the first and second wavelengths $\lambda_1$, $\lambda_2$ can correspond, for example, to the operational EMR wavelength ranges for the corresponding emitters 5256, 5258.

FIG. 30 illustrates a visualization system 5200 projecting structured light 5259 on a tissue 5210 at a surgical site, in accordance with at least one aspect of the present disclosure. The visualization system 5200 can include a receiver assembly 5206 and an emitter assembly 5204 having a single EMR source 5262, as described above in relation to FIGS. 29A and 29B. In an illustrative application, the control circuit 5202 has controlled the light valve assembly 5252 of the emitter assembly 5204 to cause the second emitter 5258 to emit structured light 5259 to display a pattern 5260 on the tissue 5210. The structured light 5259 can be emitted by the emitter assembly 5204 at any wavelength in the EMR spectrum (i.e., either visible or non-visible wavelengths). In various aspects, the control circuit 5202 can control the emitter assembly 5204 in response to a selection by a user or via automatic control from a control algorithm executed by the control circuit 5202. Further, the control circuit 5202 can be configured to cause the emitter assembly 5204 to emit the EMR (e.g., structured light 5259 as depicted) as a component of a pulse sequence for visualizing or calculating data related to the tissue 5210, as discussed above with respect to FIGS. 22-28, or maintain the structured light on the tissue 5210 to aid a surgeon in visualizing the tissue 5210 during the surgical procedure.

FIGS. 31A-31B illustrates diagrams of an emitter assembly 5204, including a single EMR source 5262, in accordance with at least one aspect of the present disclosure. In this aspect, the emitter assembly 5204 includes a single light valve 5254, as opposed to the dual light valves 5254a, 5254b as depicted in FIGS. 29A-29B. In this aspect, the control circuit 5202 is coupled to the light valve 5254 and can control the light valve 5254 to determine whether either only the first emitter 5256 is emitting EMR (e.g., visible light/IR or structured light), as depicted in FIG. 31A, or both of the emitters 5256, 5258 are emitting EMR (e.g., visible light/IR and structured light), as depicted in FIG. 31B. It should be noted that although the first emitter 5256 is depicted as emitting visible light/IR and the second emitter 5258 is depicted as emitting structured light, in other aspects, the type of EMR emitted by the emitters 5256, 5258 can be reversed or otherwise changed according to the principles discussed herein.

Combination Emitter and Camera Assembly

FIG. 32 illustrates a visualization system 5200, including a combined multispectral and structured light source and 3D camera, in accordance with at least one aspect of the present disclosure. In various aspects of the visualization system 5200, the emitter assembly can be integrated with, mounted on, clipped to, or otherwise associated with the camera assembly. For example, in one aspect, the visualization system 5200 can include a combined emitter and waveform sensor assembly, as opposed to separate emitter and waveform sensor assemblies, as depicted in, for example, FIGS. 1-2 and 9. In this aspect, the visualization system 5200 includes a first emitter 5270 that is configured to output visible light and IR (including, e.g., NIR, SWIR, and LIR) and a second emitter 5272 that is configured to output structured light (which can include structured visible light or non-visible EMR).

The EMR emitted by the first emitter 5270 can be selected to penetrate the tissue surface and tissue mass to reach critical anatomy tissue being obscurants of connective tissue for visualizing that critical anatomy tissue, as described above. Further, the visualization system 5200 includes a first waveform sensor 5274 (e.g., a first camera) and a second waveform sensor 5276 (e.g., a second camera) that are configured to detect the corresponding EMR reflected from the tissue at which the first and second emitters 5270, 5272 are directed. In aspects where the first and second waveform sensors 5274, 5276 are cameras, the first and second waveform sensors 5274, 5276 can be arranged to capture 3D images (i.e., the images captured by each camera can be combined to generate a 3D image). The first and second waveform sensors 5274, 5276 can be configured to detect or visualize coherent or incoherent visible light, IR, and/or any other EMR emitted by the first and second emitters 5270, 5272. As with the dual emitter and camera assemblies described above, the depicted visualization system 5200 is capable of allowing users to identify critical structures (e.g., ureters or blood vessels), especially when those structures are obscured by fat, connective tissue, blood, or other organs.

In the depicted aspect, the first and second emitters 5270, 5272 and the first and second waveform sensors 5274, 5276 are arranged in a roughly rhomboidal pattern, wherein the first and second emitters 5270, 5272 are positioned oppositely with respect to each other and the first and second waveform sensors 5274, 5276 are likewise positioned oppositely with respect to each other. However, the first and second emitters 5270, 5272 and the first and second waveform sensors 5274, 5276 can be arranged in a variety of other configurations and patterns such that the first and second waveform sensors 5274, 5276 are capable of receiving reflected EMR that has been emitted by the first and second emitters 5270, 5272 at a surgical site.

EXAMPLES

Various aspects of the subject matter described herein are set out in the following numbered examples:

Example 1. A surgical instrument for visualizing a surgical site. The surgical instrument comprises an emitter assembly configured to emit electromagnetic radiation at the surgical site, the electromagnetic radiation comprising at least one of infrared radiation, visible light, or structured light; a receiver assembly configured to receive the electromagnetic radiation reflected from the surgical site; and a control circuit coupled to the emitter assembly and the receiver assembly. The control circuit is configured to: cause the emitter assembly to pulse the electromagnetic radiation in a sequence comprising at least one of the infrared radiation, the visible light, or the structured light; detect reflected electromagnetic radiation corresponding to the emitted electromagnetic radiation via the receiver assembly; determine tissue information according to the reflected electromagnetic radiation; and modify the sequence at which at least one of the infrared radiation, the visible light, or the structured light is emitted by the emitter assembly according to the tissue information.

Example 2. The surgical instrument of Example 1, wherein the control circuit is configured to control the emitter assembly to sweep the emitted electromagnetic radiation over a range of wavelengths.

Example 3. The surgical instrument of Example 2, wherein the control circuit is configured to modify the sequence at which at least one of the infrared radiation, the visible light, or the structured light is emitted by the emitter assembly according to the tissue information determined at one or more wavelengths within the range of wavelengths.

Example 4. The surgical instrument of any one of Examples 1-3, wherein the tissue information comprises at least one of a distance to a tissue, a shape of the tissue, or an anatomical type of the tissue and combinations thereof.

Example 5. The surgical instrument of any one of Examples 1-4, wherein the surgical instrument comprises an end effector.

Example 6. The surgical instrument of any one of Examples 1-5, wherein the control circuit is configured to visualize a tissue on a display coupled to the control circuit according to the determined tissue information.

Example 7. The surgical instrument of Example 6, wherein the control circuit is configured to track movement of tissue structures on the display according to the determined tissue information.

Example 8. A surgical visualization system for visualizing a surgical site. The surgical visualization system comprises a control circuit configured to: cause electromagnetic radiation to be pulsed in a sequence comprising at least one of the infrared radiation, the visible light, or the structured light; extract tissue information from reflected electromagnetic radiation corresponding to the emitted electromagnetic radiation; and modify the sequence at which at least one of the infrared radiation, the visible light, or the structured light is emitted according to the tissue information.

Example 9. The surgical visualization system of Example 8, comprising an emitter assembly, wherein the control circuit is configured to control the emitter assembly to sweep the emitted electromagnetic radiation over a range of wavelengths.

Example 10. The surgical visualization system of Example 9, wherein the control circuit is configured to modify the sequence at which at least one of the infrared radiation, the visible light, or the structured light is emitted by the emitter assembly according to the tissue information determined at one or more wavelengths within the range of wavelengths.

Example 11. The surgical visualization system of any one of Examples 8-10, wherein the tissue information comprises at least one of a distance to a tissue, a shape of the tissue, or an anatomical type of the tissue and combinations thereof.

Example 12. The surgical visualization system of any one of Examples 8-11, comprising a waveform sensor assembly positioned on a surgical instrument comprising an end effector.

Example 13. The surgical visualization system of any one of Examples 8-12, wherein the control circuit is configured to visualize a tissue on a display coupled to the control circuit according to the determined tissue information.

Example 14. The surgical visualization system of Example 13, wherein the control circuit is configured to track movement of tissue structures on the display according to the determined tissue information.

Example 15. A surgical instrument for visualizing a surgical site. The surgical instrument comprises an emitter assembly configured to emit electromagnetic radiation at the surgical site, the electromagnetic radiation comprising at least one of infrared radiation, visible light, or structured light; a receiver assembly configured to receive the electromagnetic radiation reflected from the surgical site; and a control circuit coupled to the emitter assembly and the receiver assembly. The control circuit is configured to: receive a tissue type selection; cause the emitter assembly to pulse the electromagnetic radiation in a sequence corresponding to the tissue type selection, the sequence comprising at least one of the infrared radiation, the visible light, or the structured light; detect reflected electromagnetic radiation corresponding to the emitted electromagnetic radiation via the receiver assembly; and determine tissue information according to the reflected electromagnetic radiation.

Example 16. The surgical instrument of Example 15, wherein the sequence corresponding to the tissue type selection is configured for visualizing the tissue type selection.

Example 17. The surgical instrument of Example 15 or 16, wherein the tissue information comprises at least one of a distance to a tissue, a shape of the tissue, or an anatomical type of the tissue and combinations thereof.

Example 18. The surgical instrument of any one of Examples 15-17, wherein the surgical instrument comprises an end effector.

Example 19. The surgical instrument of any one of Examples 15-18, wherein the control circuit is configured to visualize a tissue on a display coupled to the control circuit according to the determined tissue information.

Example 20. The surgical instrument of Example 19, wherein the control circuit is configured to track movement of tissue structures on the display according to the determined tissue information.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical instrument for visualizing a surgical site, the surgical instrument comprising:
   an emitter assembly configured to emit electromagnetic radiation at the surgical site, the electromagnetic radiation comprising infrared radiation and visible light;
   a receiver assembly configured to receive electromagnetic radiation reflected from the surgical site, wherein the reflected electromagnetic radiation corresponds to the emitted electromagnetic radiation; and
   a control circuit coupled to the emitter assembly and the receiver assembly, the control circuit configured to:
      cause the emitter assembly to pulse the electromagnetic radiation in a predetermined sequence comprising the infrared radiation and the visible light, wherein the predetermined sequence corresponds to a preselected tissue type;
      detect reflected electromagnetic radiation corresponding to the emitted electromagnetic radiation via the receiver assembly;
      determine tissue information according to the reflected electromagnetic radiation; and
      modify the predetermined sequence in which the infrared radiation and the visible light are emitted by the emitter assembly according to the tissue information;
   wherein causing the emitter assembly to pulse the electromagnetic radiation in a predetermined sequence comprising the infrared radiation and the visible light comprises emitting the infrared radiation for a first predetermined length of time, emitting the visible light for a second predetermined length of time, and emitting the infrared radiation and the visible light in a predetermined order;
   wherein emitting the infrared radiation and the visible light in the predetermined order comprises emitting the infrared radiation before emitting the visible light, wherein modifying the predetermined sequence comprises modifying the predetermined sequence to a second sequence in which the visible light is emitted before the infrared radiation, and wherein the control circuit is further configured to cause the emitter assembly to pulse the electromagnetic radiation in the second sequence based on the modification.

2. The surgical instrument of claim 1, wherein the control circuit is configured to control the emitter assembly to sweep the emitted electromagnetic radiation over a range of wavelengths.

3. The surgical instrument of claim 2, wherein the control circuit is configured to modify the predetermined sequence in which the infrared radiation and the visible light are emitted by the emitter assembly according to the tissue information, wherein the tissue information is determined according to one or more wavelengths within the range of wavelengths.

4. The surgical instrument of claim 1, wherein the tissue information comprises at least one of a distance to a tissue, a shape of the tissue, or an anatomical type of the tissue and combinations thereof.

5. The surgical instrument of claim 1, wherein the surgical instrument comprises an end effector comprising a first jaw and a second jaw, and wherein the end effector comprises the emitter assembly and the receiver assembly.

6. The surgical instrument of claim 1, wherein the control circuit is configured to visualize a tissue on a display coupled to the control circuit according to the determined tissue information.

7. The surgical instrument of claim 6, wherein the control circuit is configured to track movement of tissue structures on the display according to the determined tissue information.

8. The surgical instrument of claim 6, wherein the control circuit is configured to distinguish the preselected tissue type from other tissue on the display.

9. The surgical instrument of claim 1, wherein the preselected tissue type comprises one of a plurality of tissue types stored in a memory.

10. The surgical instrument of claim 1, wherein modifying the predetermined sequence comprises modifying the first predetermined length of time, the second predetermined length of time, and the predetermined order of the infrared radiation and the visible light.

11. The surgical instrument of claim 1, wherein the determined tissue information comprises a tissue type, and wherein modifying the predetermined sequence comprises modifying the predetermined order of the infrared radiation and the visible light according to the tissue type.

12. A surgical visualization system for visualizing a surgical site, the surgical visualization system comprising a control circuit configured to:
cause electromagnetic radiation to be pulsed in a predetermined sequence comprising infrared radiation and visible light, wherein the predetermined sequence corresponds to a preselected tissue type;
extract tissue information from reflected electromagnetic radiation corresponding to the emitted electromagnetic radiation; and
modify the predetermined sequence in which the infrared radiation and the visible light are emitted according to the tissue information;
wherein causing electromagnetic radiation to be pulsed in a predetermined sequence comprising infrared radiation and visible light comprises emitting the infrared radiation for a first predetermined length of time, emitting the visible light for a second predetermined length of time, and emitting the infrared radiation and the visible light in a predetermined order;
wherein emitting the infrared radiation and the visible light in the predetermined order comprises emitting the visible light before the infrared radiation, wherein modifying the predetermined sequence comprises modifying the predetermined sequence to a second sequence in which the infrared radiation is emitted before the visible light, and wherein the control circuit is further configured to cause the electromagnetic radiation to be pulsed in the second sequence based on the modification.

13. The surgical visualization system of claim 12, comprising an emitter assembly, wherein the control circuit is configured to control the emitter assembly to sweep the emitted electromagnetic radiation over a range of wavelengths.

14. The surgical visualization system of claim 13, wherein the control circuit is configured to modify the predetermined sequence in which the infrared radiation and the visible light are emitted by the emitter assembly according to the tissue information, wherein the tissue information is determined according to one or more wavelengths within the range of wavelengths.

15. The surgical visualization system of claim 12, wherein the tissue information comprises at least one of a distance to a tissue, a shape of the tissue, or an anatomical type of the tissue and combinations thereof.

16. The surgical visualization system of claim 12, comprising a waveform sensor assembly positioned on a surgical instrument comprising an end effector.

17. The surgical visualization system of claim 12, wherein the control circuit is configured to visualize a tissue on a display coupled to the control circuit according to the determined tissue information.

18. The surgical visualization system of claim 17, wherein the control circuit is configured to track movement of tissue structures on the display according to the determined tissue information.

19. The surgical visualization system of claim 12, wherein the preselected tissue type comprises one of a plurality of tissue types stored in a memory.

20. A surgical instrument for visualizing a surgical site, the surgical instrument comprising:
an emitter assembly configured to emit electromagnetic radiation at the surgical site, the electromagnetic radiation comprising more than one wavelength, the more than one wavelength comprising a first wavelength and a second wavelength;
a receiver assembly configured to receive electromagnetic radiation reflected from the surgical site, wherein the reflected electromagnetic radiation corresponds to the emitted electromagnetic radiation; and
a control circuit coupled to the emitter assembly and the receiver assembly, the control circuit configured to:
receive a tissue type selection;
cause the emitter assembly to pulse the electromagnetic radiation in a preselected sequence corresponding to the tissue type selection, the preselected sequence comprising the more than one wavelength;
detect reflected electromagnetic radiation corresponding to the emitted electromagnetic radiation via the receiver assembly;
determine tissue information according to the reflected electromagnetic radiation; and
cause the emitter assembly to emit the second wavelength before the first wavelength based on the determined tissue information;
wherein causing the emitter assembly to pulse the electromagnetic radiation in a preselected sequence corresponding to the tissue type selection comprises emitting each wavelength of the more than one wavelength a predetermined length of time and in a predetermined order, and wherein emitting each wavelength of the more than one wavelength in a predetermined order comprises emitting the first wavelength before the second wavelength.

21. The surgical instrument of claim 20, wherein the preselected sequence corresponding to the tissue type selection is configured for visualizing the tissue type selection.

22. The surgical instrument of claim 20, wherein the tissue information comprises at least one of a distance to a tissue, a shape of the tissue, or an anatomical type of the tissue and combinations thereof.

23. The surgical instrument of claim 20, wherein the surgical instrument comprises an end effector.

24. The surgical instrument of claim 20, wherein the control circuit is configured to visualize a tissue on a display coupled to the control circuit according to the determined tissue information.

25. The surgical instrument of claim 24, wherein the control circuit is configured to track movement of tissue structures on the display according to the determined tissue information.

26. The surgical instrument of claim 20, wherein the tissue type selection comprises one of a plurality of tissue types stored in a memory.

27. A surgical system, comprising:
- an emitter assembly configured to emit electromagnetic radiation at a surgical site, the electromagnetic radiation comprising a first wavelength, a second wavelength, and a third wavelength;
- a receiver assembly configured to receive electromagnetic radiation reflected from the surgical site, wherein the reflected electromagnetic radiation corresponds to the emitted electromagnetic radiation; and
- a control circuit coupled to the emitter assembly and the receiver assembly, the control circuit configured to:
  - cause the emitter assembly to pulse the first wavelength, the second wavelength, and the third wavelength in a first order;
  - detect reflected electromagnetic radiation corresponding to the emitted electromagnetic radiation via the receiver assembly;
  - determine tissue information according to the reflected electromagnetic radiation; and
  - cause the emitter assembly to pulse the first wavelength, the second wavelength, and the third wavelength in a second order different than the first order based on the tissue information.

\* \* \* \* \*